US009271764B2

(12) United States Patent
Sheffer et al.

(10) Patent No.: US 9,271,764 B2
(45) Date of Patent: *Mar. 1, 2016

(54) INTERSPINOUS SPACER WITH DEPLOYABLE MEMBERS AND RELATED METHOD

(71) Applicant: EBI, LLC, Parsippany, NJ (US)

(72) Inventors: Garrett A. Sheffer, Hoboken, NJ (US); Juan Antonio Hervas-Presencia, Valencia (ES); Gustavo Pellicer Alcazar, Valencia (ES); Miguel Albert Alarcon, Valencia (ES)

(73) Assignee: EBI, LLC, Parsippany, NJ (US)

( * ) Notice: Subject to any disclaimer, the term of this patent is extended or adjusted under 35 U.S.C. 154(b) by 58 days.

This patent is subject to a terminal disclaimer.

(21) Appl. No.: 13/757,881

(22) Filed: Feb. 4, 2013

(65) Prior Publication Data

US 2013/0144340 A1 Jun. 6, 2013

Related U.S. Application Data

(63) Continuation of application No. 12/700,426, filed on Feb. 4, 2010, now Pat. No. 8,388,656.

(51) Int. Cl.
*A61B 17/70* (2006.01)
(52) U.S. Cl.
CPC ......... *A61B 17/7062* (2013.01); *A61B 17/7065* (2013.01)
(58) Field of Classification Search
USPC ................................................ 606/248–249
See application file for complete search history.

(56) References Cited

U.S. PATENT DOCUMENTS

| 5,314,477 A | 5/1994 | Marnay |
| 5,645,599 A | 7/1997 | Samani |
| 5,683,464 A | 11/1997 | Wagner et al. |
| 5,885,299 A | 3/1999 | Winslow et al. |

(Continued)

FOREIGN PATENT DOCUMENTS

| EP | 1330987 A1 | 7/2003 |
| EP | 1945117 A2 | 7/2008 |

(Continued)

OTHER PUBLICATIONS

"U.S. Appl. No. 11/746,204, Non Final Office Action mailed Jul. 6, 2011", 16 pgs.

(Continued)

*Primary Examiner* — Jan Christopher Merene
(74) *Attorney, Agent, or Firm* — Schwegman Lundberg & Woessner, P.A.

(57) ABSTRACT

The present teachings provide one or more surgical implements for repairing damaged tissue, such as in the case of spinal stenosis. An implant for insertion between adjacent spinous processes is provided. The implant can include a body having a first end, a second end and defining a bore. The implant can include a first cap coupled to the first end of the body, a second cap coupled to the second end of the body, with each of the caps defining a space. The implant can include a connector coupled to the first cap and the second cap through the bore. The implant can include at least one deployable member coupled to the first end of the body and the first cap. The at least one deployable member can be retained within the first space in a first position, and can extend from the first space in a second position.

25 Claims, 17 Drawing Sheets

(56) References Cited

U.S. PATENT DOCUMENTS

| | | | |
|---|---|---|---|
| 6,139,579 A | 10/2000 | Steffee et al. | |
| 6,238,397 B1 | 5/2001 | Zucherman et al. | |
| 6,293,949 B1 | 9/2001 | Justis et al. | |
| 6,419,676 B1 | 7/2002 | Zucherman et al. | |
| 6,440,169 B1 | 8/2002 | Elberg et al. | |
| 6,626,943 B2 | 9/2003 | Eberlein | |
| 6,743,257 B2 | 6/2004 | Castro | |
| 6,761,719 B2 | 7/2004 | Justis et al. | |
| 7,011,685 B2 | 3/2006 | Arnin et al. | |
| 7,108,697 B2 | 9/2006 | Mingozzi et al. | |
| 7,497,859 B2 | 3/2009 | Zucherman et al. | |
| 7,753,938 B2 | 7/2010 | Aschmann et al. | |
| 8,388,656 B2 | 3/2013 | Sheffer et al. | |
| 2004/0106995 A1 | 6/2004 | Le Couedic et al. | |
| 2005/0125063 A1 | 6/2005 | Matge et al. | |
| 2005/0131412 A1 | 6/2005 | Olevsky et al. | |
| 2005/0203624 A1 | 9/2005 | Serhan et al. | |
| 2005/0261768 A1 | 11/2005 | Trieu | |
| 2005/0273100 A1 | 12/2005 | Taylor | |
| 2006/0015181 A1 | 1/2006 | Elberg | |
| 2006/0084988 A1 | 4/2006 | Kim | |
| 2006/0085070 A1 | 4/2006 | Kim | |
| 2006/0149278 A1 | 7/2006 | Abdou | |
| 2006/0184171 A1 | 8/2006 | Biedermann et al. | |
| 2006/0271049 A1 | 11/2006 | Zucherman et al. | |
| 2007/0032790 A1 | 2/2007 | Aschmann et al. | |
| 2007/0043361 A1 | 2/2007 | Malandain et al. | |
| 2007/0049935 A1 | 3/2007 | Edidin et al. | |
| 2007/0106298 A1 | 5/2007 | Carli et al. | |
| 2007/0161992 A1 | 7/2007 | Kwak et al. | |
| 2007/0161993 A1 | 7/2007 | Lowery et al. | |
| 2007/0162000 A1 | 7/2007 | Perkins | |
| 2007/0162001 A1 | 7/2007 | Chin et al. | |
| 2007/0162002 A1 | 7/2007 | Tornier | |
| 2007/0162003 A1 | 7/2007 | Tornier et al. | |
| 2007/0162004 A1 | 7/2007 | Tornier et al. | |
| 2007/0162005 A1 | 7/2007 | Peterson et al. | |
| 2007/0191837 A1 | 8/2007 | Trieu | |
| 2007/0225706 A1 | 9/2007 | Clark et al. | |
| 2007/0233076 A1 | 10/2007 | Trieu | |
| 2007/0260245 A1 | 11/2007 | Malandain et al. | |
| 2007/0265623 A1 | 11/2007 | Malandain | |
| 2007/0276373 A1 | 11/2007 | Malandain | |
| 2007/0282340 A1 | 12/2007 | Malandain | |
| 2008/0147190 A1 | 6/2008 | Dewey et al. | |
| 2008/0147192 A1 | 6/2008 | Edidin et al. | |
| 2008/0161818 A1 | 7/2008 | Kloss et al. | |
| 2008/0177306 A1* | 7/2008 | Lamborne et al. | 606/246 |
| 2008/0255668 A1 | 10/2008 | Fallin et al. | |
| 2008/0262622 A1 | 10/2008 | Butler | |
| 2008/0281423 A1* | 11/2008 | Sheffer et al. | 623/17.11 |
| 2008/0294200 A1 | 11/2008 | Kohm et al. | |
| 2009/0012528 A1 | 1/2009 | Aschmann et al. | |
| 2009/0054988 A1 | 2/2009 | Hess | |
| 2009/0054989 A1 | 2/2009 | Baumgartner et al. | |
| 2009/0234389 A1 | 9/2009 | Chuang et al. | |
| 2009/0254122 A1 | 10/2009 | Khalife | |
| 2009/0264927 A1 | 10/2009 | Ginsberg et al. | |
| 2009/0265006 A1 | 10/2009 | Seifert et al. | |
| 2009/0270919 A1 | 10/2009 | Dos Reis, Jr. | |
| 2009/0292316 A1* | 11/2009 | Hess | 606/249 |
| 2010/0114166 A1* | 5/2010 | Kohm et al. | 606/247 |
| 2011/0029021 A1 | 2/2011 | Hartsell et al. | |
| 2011/0046674 A1* | 2/2011 | Calvosa et al. | 606/249 |

FOREIGN PATENT DOCUMENTS

| | | |
|---|---|---|
| EP | 1994901 A1 | 11/2008 |
| WO | WO-2006110578 A2 | 10/2006 |
| WO | WO-2007134113 A2 | 11/2007 |
| WO | WO-2008136877 A1 | 11/2008 |
| WO | WO 2009098536 A1 * | 8/2009 |

OTHER PUBLICATIONS

"U.S. Appl. No. 12/700,426, Final Office Action mailed Sep. 6, 2012", 12 pgs.

"U.S. Appl. No. 12/700,426, Non Final Office Action mailed Dec. 15, 2011", 21 pgs.

"U.S. Appl. No. 12/700,426, Notice of Allowance mailed Oct. 31, 2012", 8 pgs.

"U.S. Appl. No. 12/700,426, Response filed Jun. 15, 2012 to Non Final Office Action mailed Dec. 15, 2011", 18 pgs.

"U.S. Appl. No. 12/700,426, Response filed Oct. 17, 2012 to Final Office Action mailed Sep. 6, 2012", 13 pgs.

"U.S. Appl. No. 12/700,426, Response filed Dec. 7, 2011 to Restriction Requirement mailed Nov. 7, 2011", 3 pgs.

"U.S. Appl. No. 12/700,426, Restriction Requirement mailed Nov. 7, 2011", 6 pgs.

"European Application Serial No. 08251646.9, Partial European Search Report mailed Aug. 25, 2008", 6 pgs.

* cited by examiner

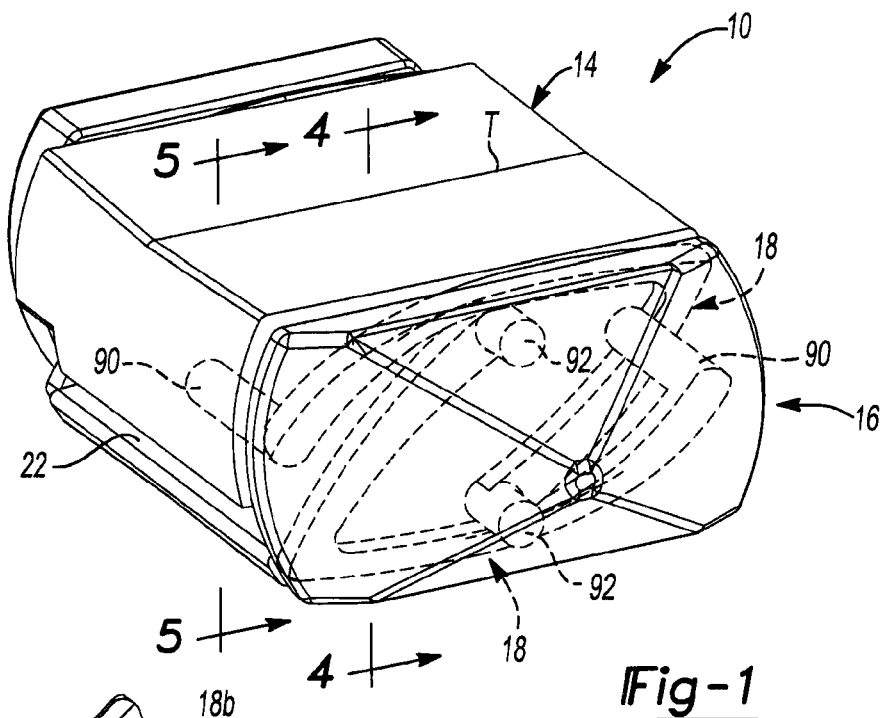
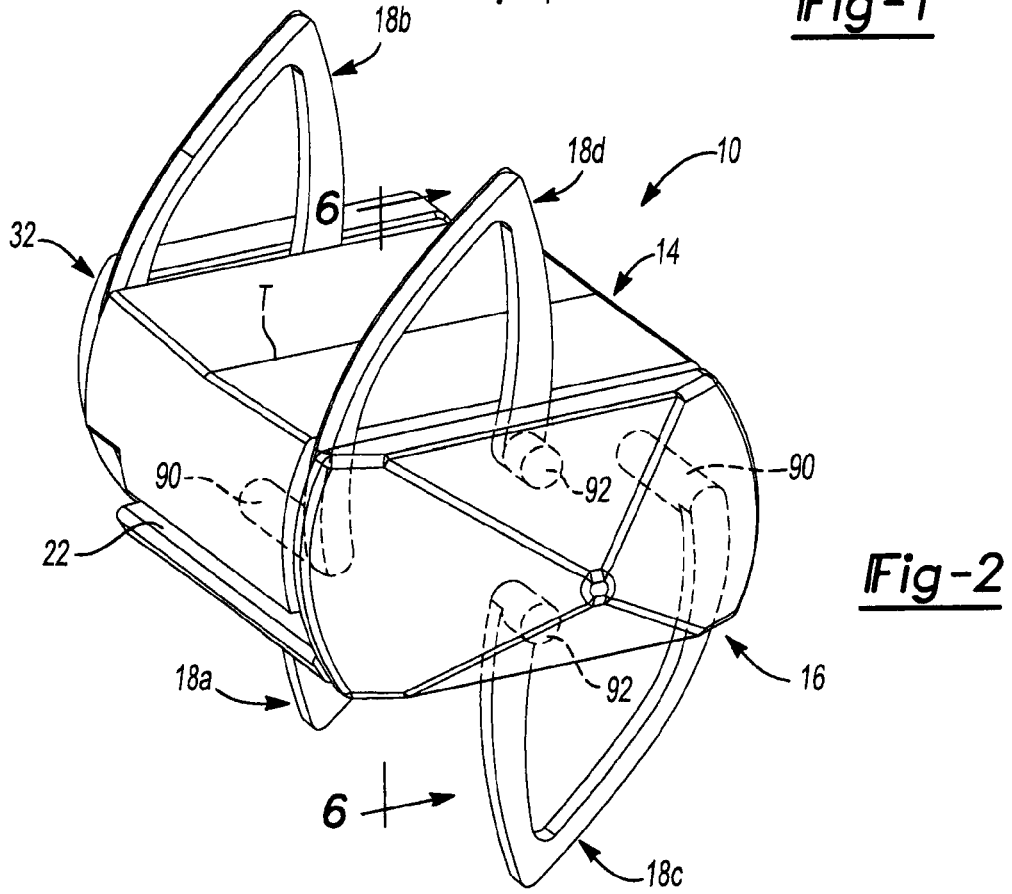

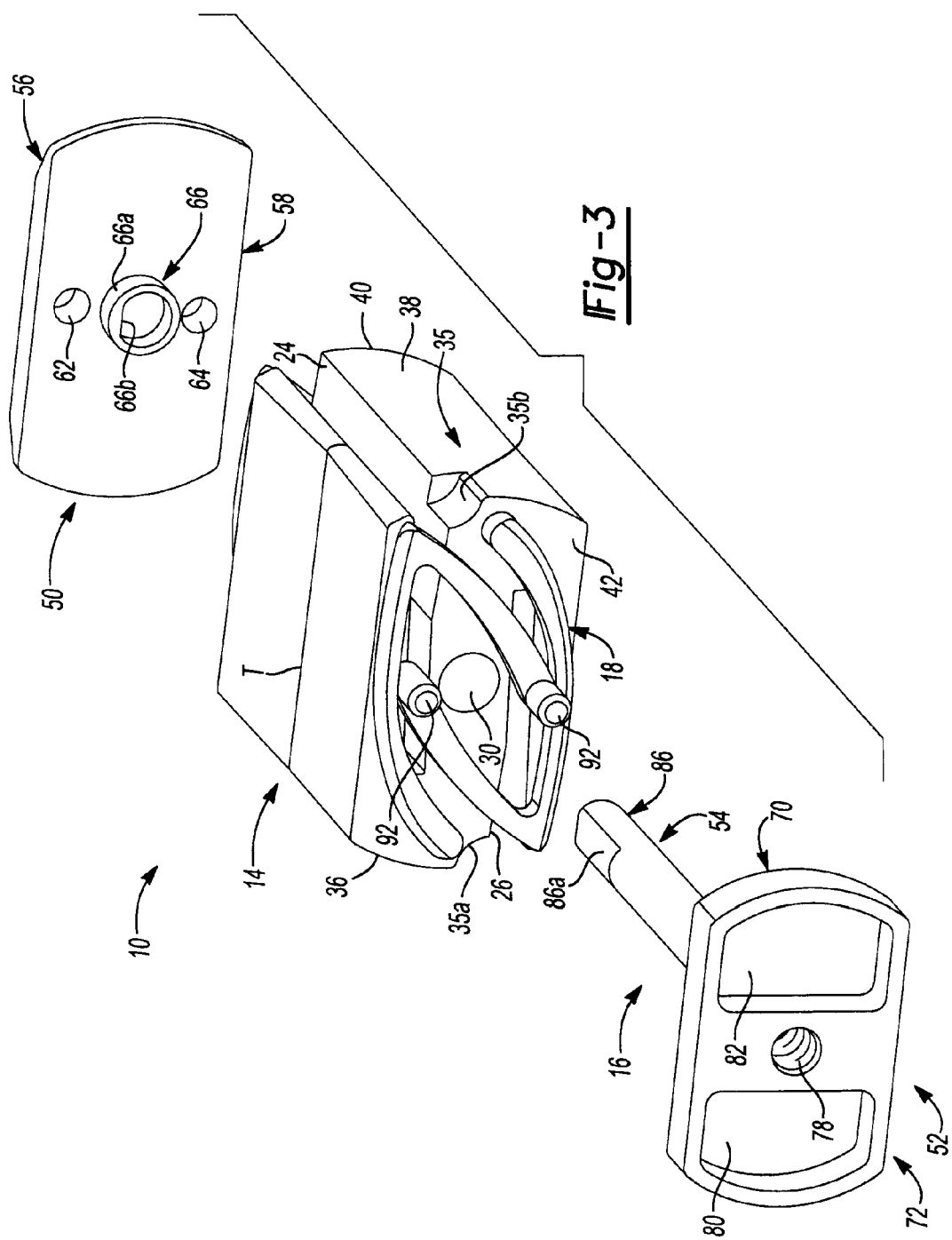

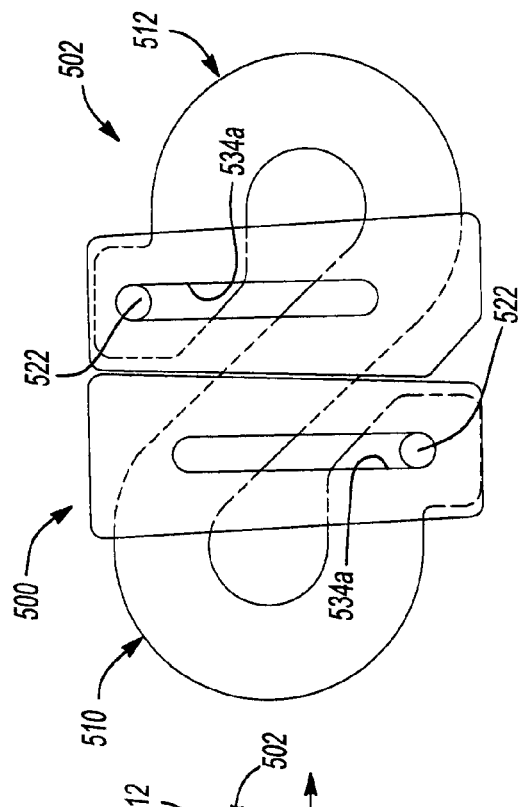
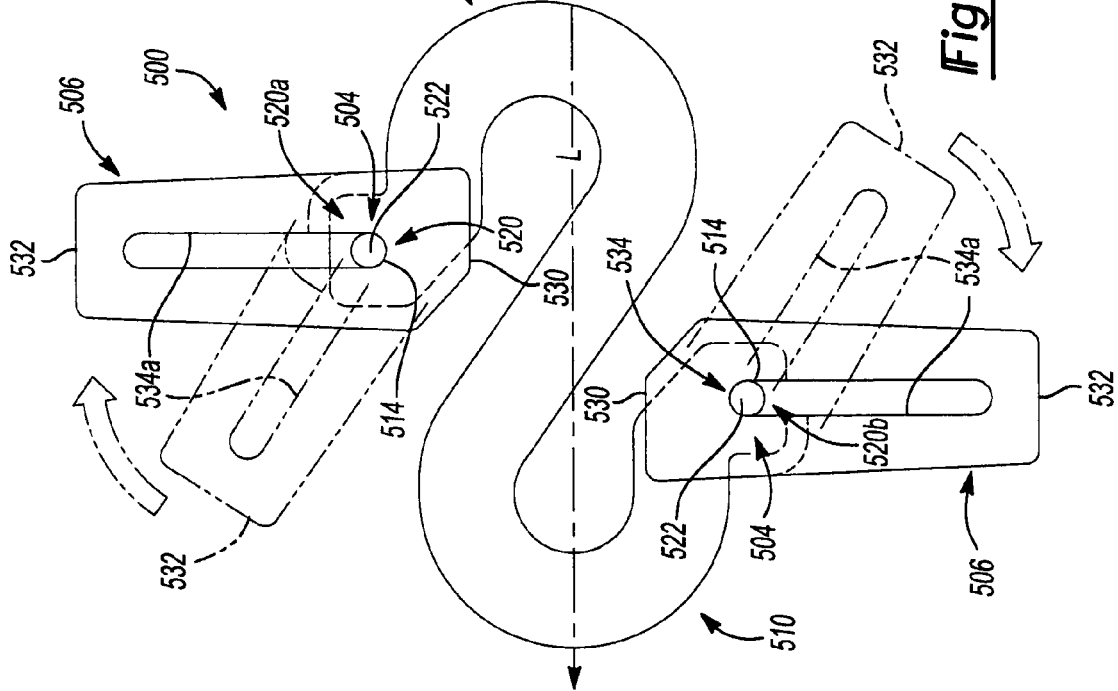

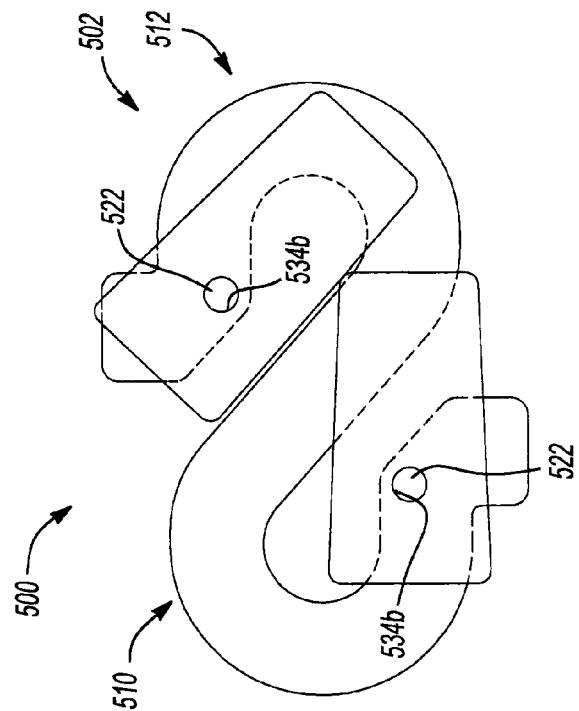
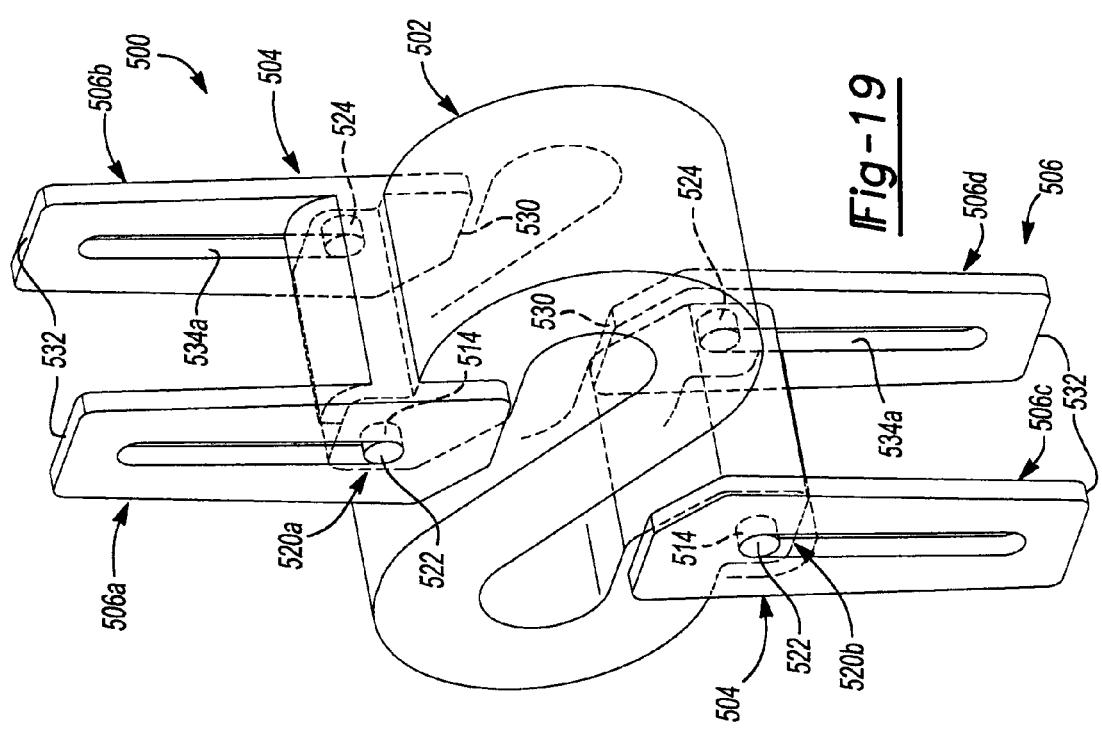

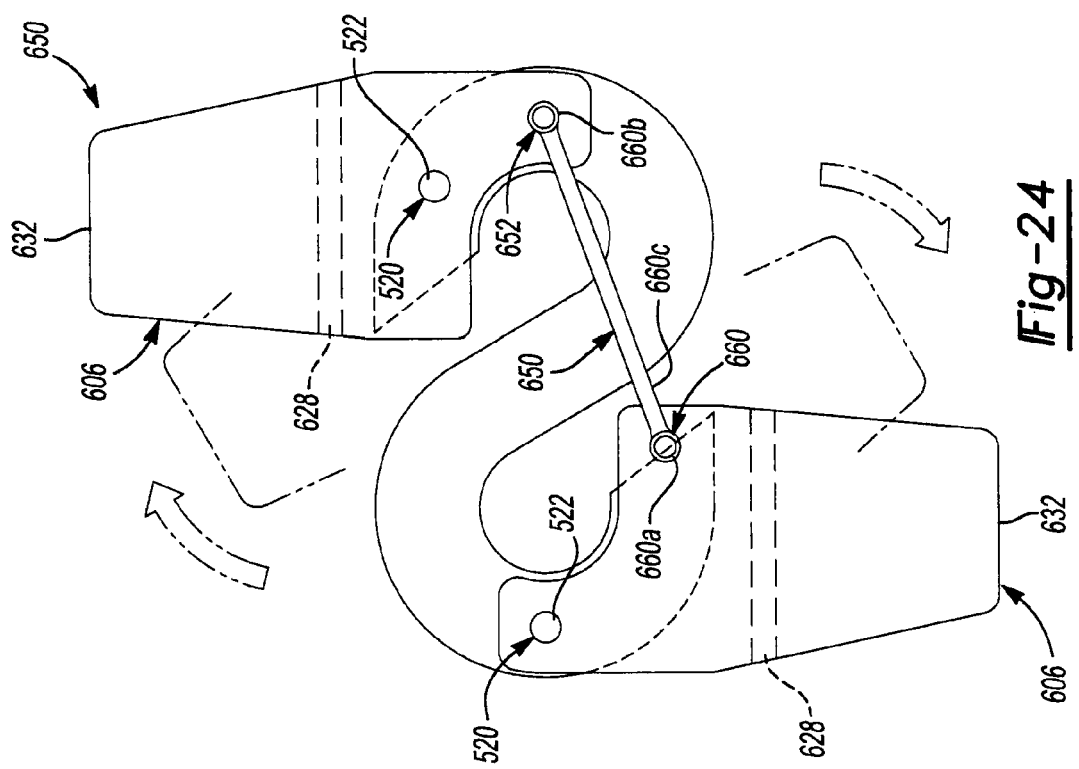
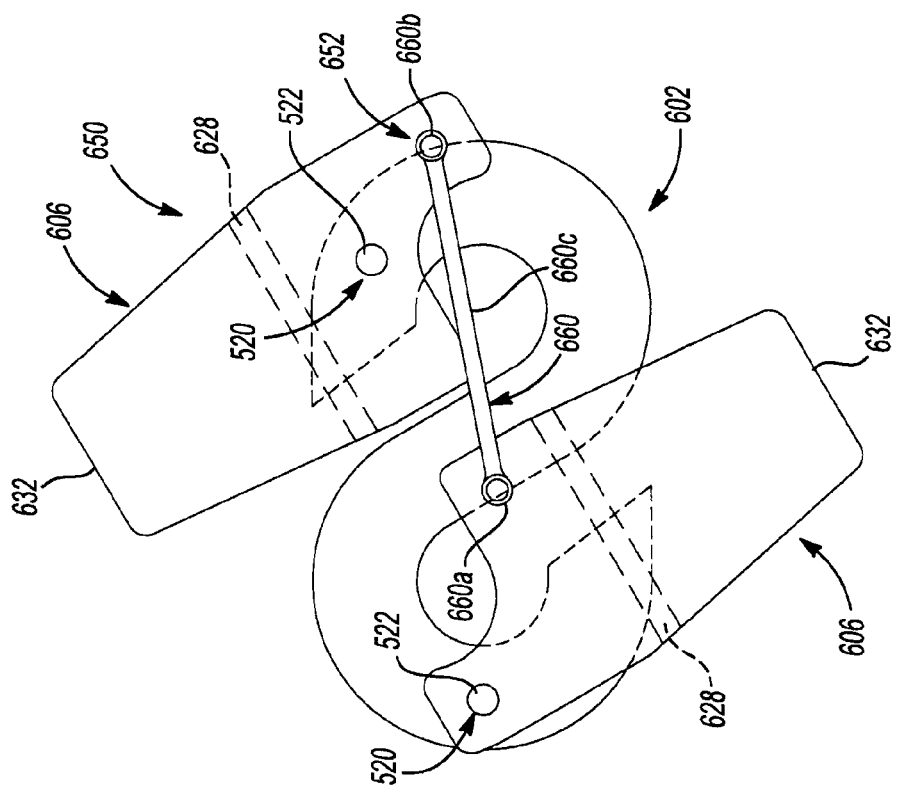

INTERSPINOUS SPACER WITH DEPLOYABLE MEMBERS AND RELATED METHOD

CROSS-REFERENCE TO RELATED APPLICATIONS

This application is a continuation of U.S. patent application Ser. No. 12/700,426, now U.S. Pat. No. 8,388,656, which was filed on Feb. 4, 2010, the entire disclosure of which is incorporated herein by reference.

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic prosthesis, such as orthopedic nails, screws, implants, etc., to restore function to the damaged tissue.

For example, damage or degeneration of one or more vertebrae can result in a narrowing of a foramen associated with the vertebrae, or spinal stenosis. Spinal stenosis can result in compression of one or more nerves associated with the vertebrae. In one example, a spinal implant can be inserted between adjacent spinous processes to distract the vertebrae, and restore the spacing of the foramen. The present teachings provide a method and apparatus for repairing damaged tissue, such as an interspinous spacer for repairing spinal stenosis.

An implant for insertion between adjacent spinous processes is provided. The implant can include a body having a first end and a second end. The body can define a bore. The implant can include a first cap coupled to the first end of the body, which can define a first space. The implant can also include a second cap, which can be coupled to the second end of the body. The second cap can define a second space. The implant can further include a connector, which can be rotatable within the bore and coupled to the first cap and the second cap so that rotation of one of the first cap or the second cap rotates the other one of the first cap and second cap. The implant can include at least one deployable member coupled to the first end of the body and the first cap. The at least one deployable member can be retained within the first space in a first, retracted position, and can extend from the first space in a second, deployed position. The rotation of the one of the first cap or the second cap relative to the body can move the at least one deployable member from the first, retracted position to the second, deployed position while maintaining the second space.

Further provided is an implant for insertion between adjacent spinous processes. The implant can include a body having a first end, a second end, and a first surface opposite a second surface. The body can define a central throughbore. The first surface and the second surface of the body can be adapted to support a respective one of the spinous processes. The implant can include an actuator system coupled to the body via the central throughbore. The actuator system can be rotatable relative to the body. The implant can also include at least one first deployable member, which can be coupled to the first end of the body. The at least one first deployable member can be movable between a first, retracted position, and a second, deployed position. The implant can include at least one second deployable member, which can be coupled to the second end of the body. The at least one second deployable member can be movable between a first, retracted position, and a second, deployed position. The rotation of the actuator system relative to the body can move the at least one first deployable member and at least one second deployable member from the first, retracted position to the second, deployed position.

Also provided is a method of using the above described implant that comprises providing an insertion instrument having a fastening member and a deployment member that are rotatable relative to a housing. The method can also include coupling the fastening member to the one of the first cap or the second cap, and coupling the deployment member to the one of the first cap or the second cap. The method can include coupling the housing of the insertion member to the body, and positioning the implant within an anatomy. The method can further include rotating the deployment member relative to the fastening member and the housing to rotate the one of the first cap or second cap relative to the body to move the at least one deployable member from the first, retracted position to the second, deployed position.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 1 is a schematic illustration of an interspinous spacer according to the present teachings in a first, retracted state;

FIG. 2 is a schematic environmental illustration of the interspinous spacer of FIG. 1 in a second, deployed state;

FIG. 3 is a partially-exploded schematic illustration of the interspinous spacer of FIG. 1;

FIG. 18 is a schematic illustration of another exemplary interspinous spacer according to one of various teachings that is movable between a first, retracted state and a second, deployed state;

FIG. 18A is a schematic illustration the interspinous spacer of FIG. 18 in the first, retracted state;

FIG. 19 is a schematic illustration of the interspinous spacer of FIG. 18 in the second, deployed state;

FIG. 20 is a schematic illustration of an alternative configuration for the interspinous spacer of FIG. 18 in the first, retracted state;

FIG. 23 is a schematic illustration of another exemplary interspinous spacer according to one of various teachings that is movable between a first, retracted state and a second, deployed state;

FIG. 24 is a schematic illustration of the interspinous spacer of FIG. 23 in the second, deployed state;

DESCRIPTION OF VARIOUS ASPECTS

Figure 3A:
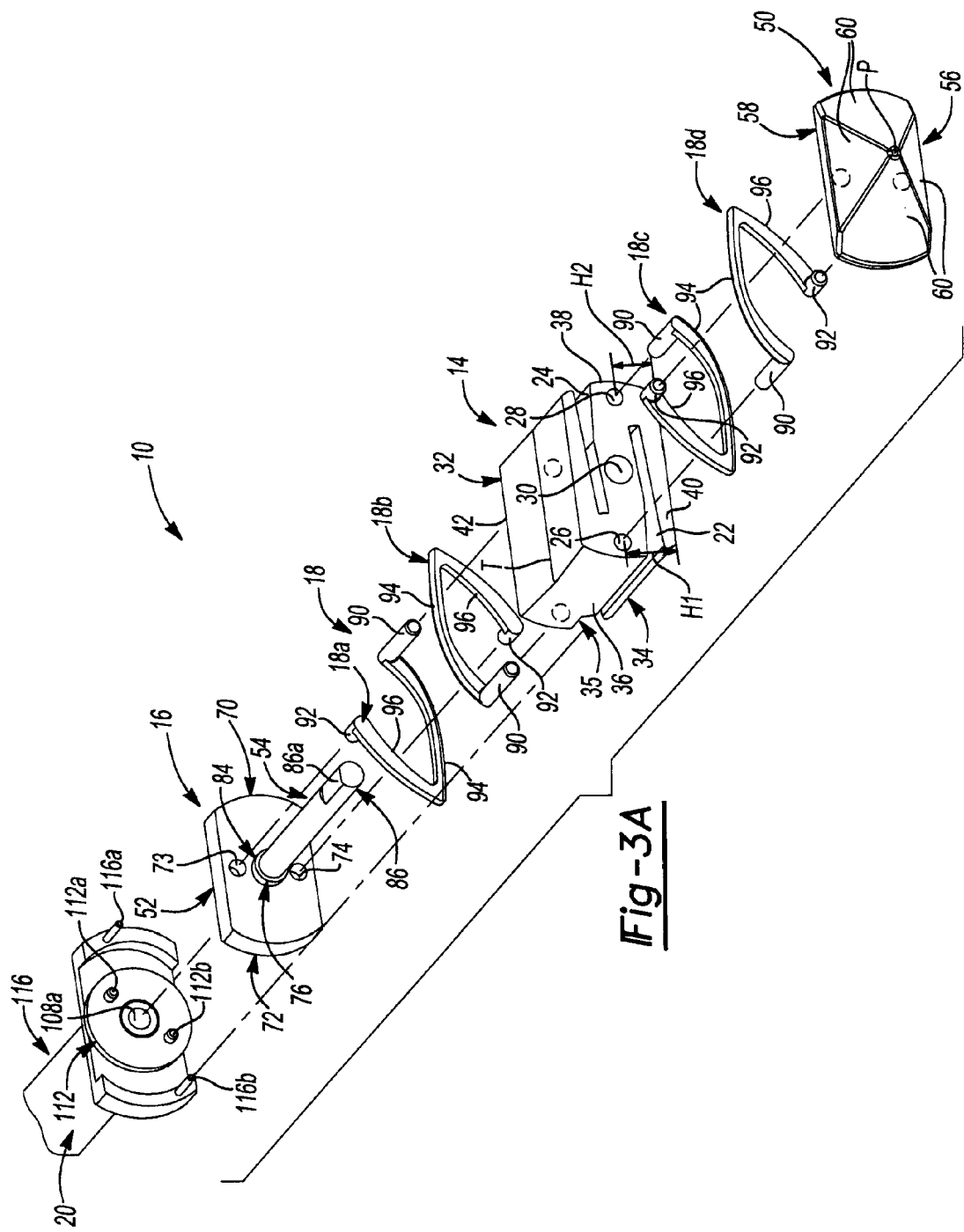
FIG. 3A is another exploded schematic illustration of the interspinous spacer of FIG. 1, operatively illustrated with a tool for moving the interspinous spacer between the first, retracted state and the second, deployed state.

The following description is merely exemplary in nature and is not intended to limit the present teachings, application, or uses. It should be understood that throughout the drawings, corresponding reference numerals indicate like or corresponding parts and features. Although the following description is related generally to a method and apparatus for use in an anatomy to repair damaged tissue, such as in the case of spinal stenosis, it will be understood that the method and apparatus as described and claimed herein, can be used in any appropriate surgical procedure, such as in a spinal fixation procedure. Therefore, it will be understood that the following discussions are not intended to limit the scope of the present teachings and claims herein.

Figure 8:
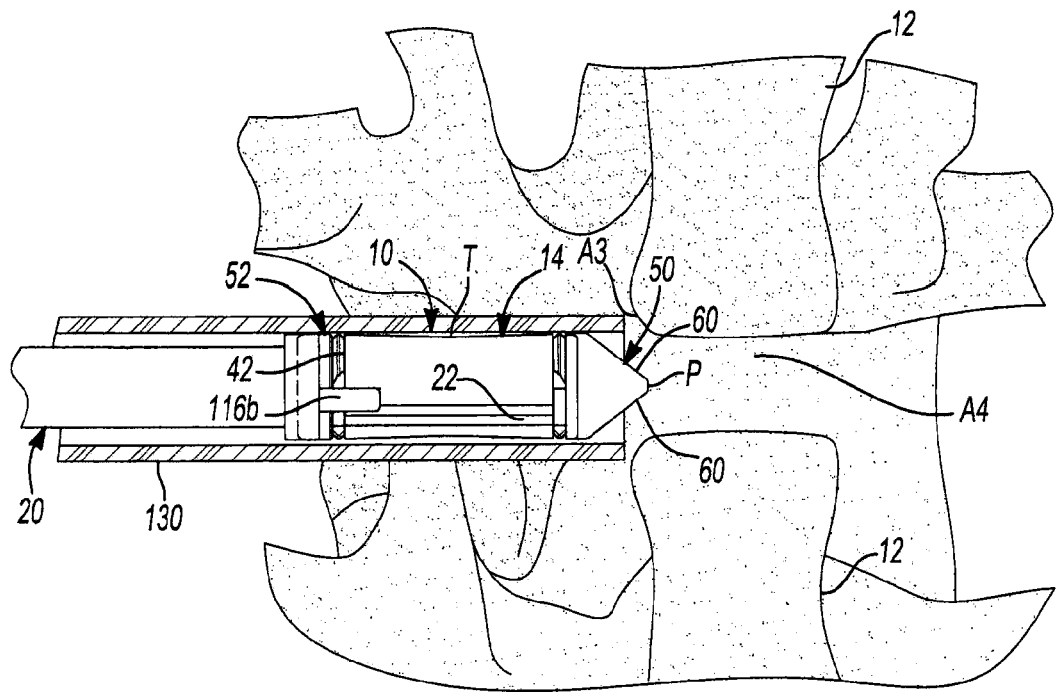
FIG. 8 is a schematic environmental illustration of a step of one of various methods for inserting the interspinous spacer into an anatomy.
Figure 9:
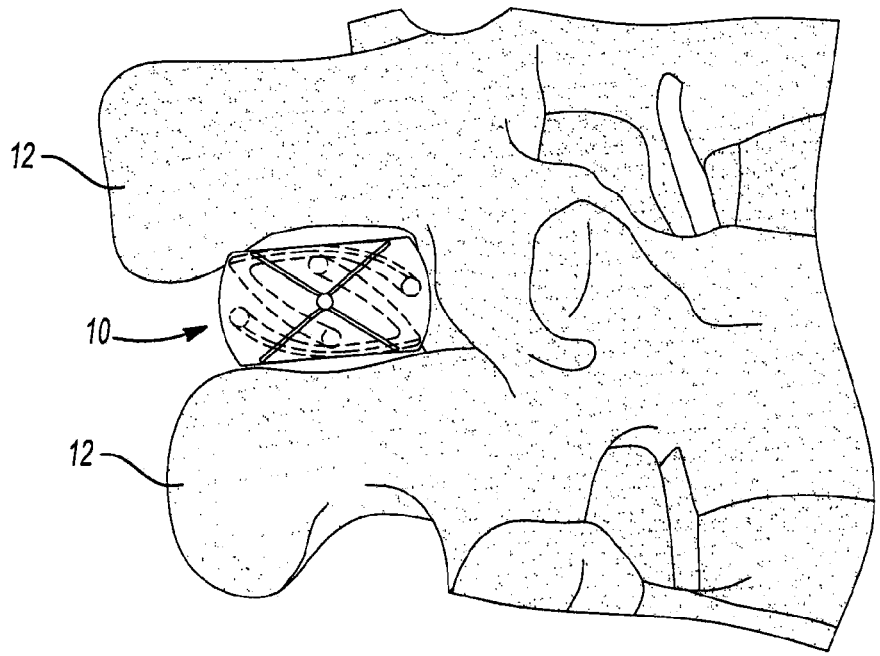
FIG. 9 is a side schematic environmental view of the interspinous spacer positioned between adjacent spinous processes in the first, retracted state.
Figure 10:
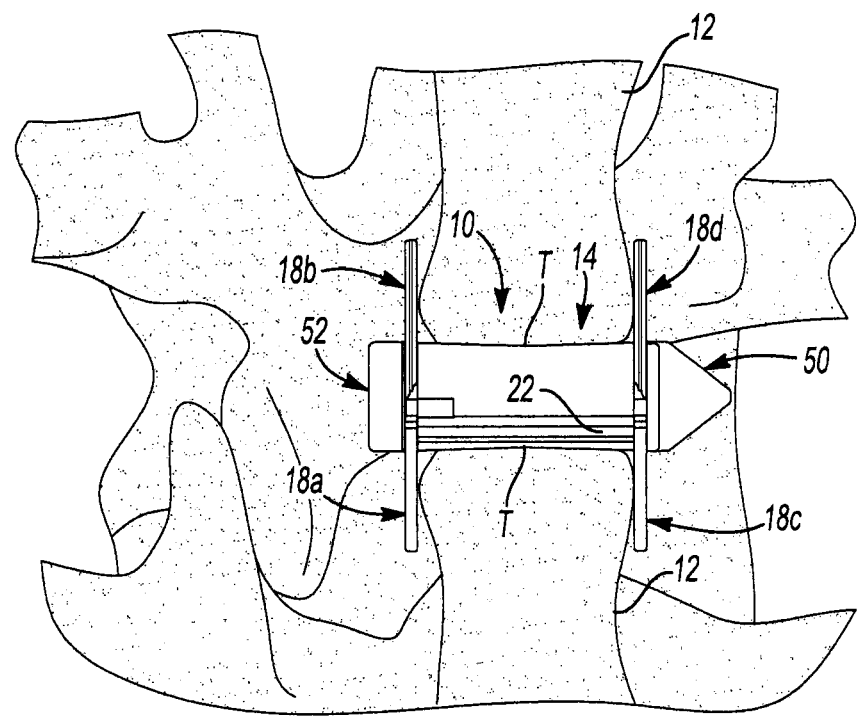
FIG. 10 is a schematic environmental illustration of the interspinous spacer positioned between adjacent spinous processes in the second, deployed state.
Figure 11:
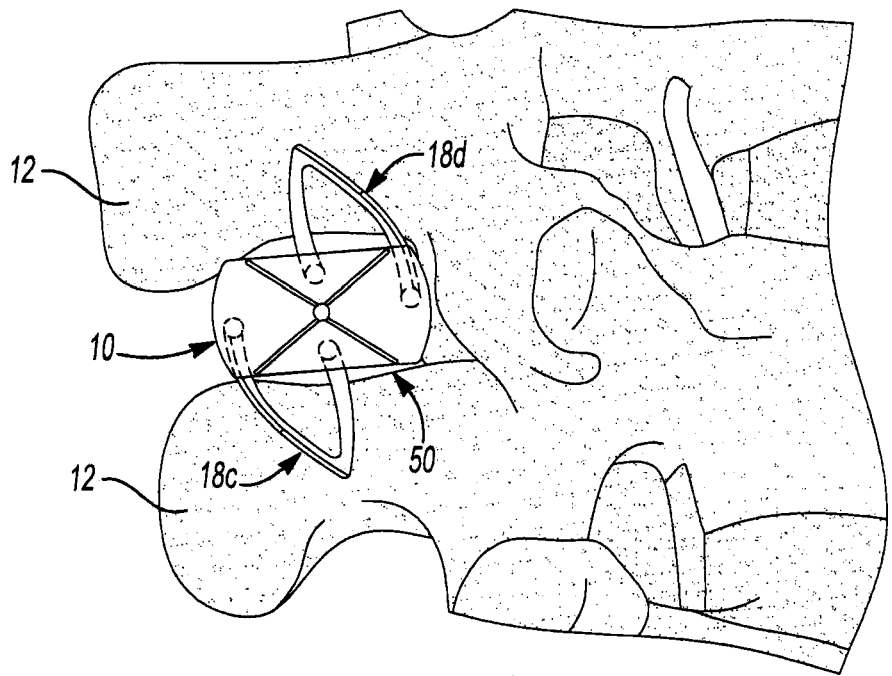
FIG. 11 is a side schematic environmental view of the interspinous spacer positioned between adjacent spinous processes in the second, deployed state.

With reference to FIGS. 1-11, an interspinous implant or spacer 10 is shown. The interspinous spacer 10 can be used to maintain spacing between adjacent vertebrae, or spinous processes 12 (FIGS. 10 and 11). In certain applications, the interspinous spacer 10 can be positioned between adjacent spinous processes 12 in a lumbar region of the spine, however, the interspinous spacer 10 can be used in other anatomical locations besides the spine. In addition, as will be discussed herein, the interspinous spacer 10 can be shaped such that the interspinous spacer 10 acts as a tension spring, which can allow for more natural motion of a patient. In one example, the interspinous spacer 10 can be used as a dilator or spacer between the adjacent spinous processes 12.

Although a single interspinous spacer 10 is illustrated and described herein as being positioned between a single pair of adjacent spinous processes 12, it should be understood that any number of interspinous spacers 10 could be positioned between any suitable pair of spinous processes 12. Further, although a single interspinous spacer 10 is illustrated and described herein as being positioned between a single pair of adjacent spinous processes 12, it should be understood that any number of interspinous spacers 10 could be positioned between the single pair of spinous processes 12. In addition, if more than one interspinous spacer 10 is employed in the anatomy, the interspinous spacers 10 can be coupled or connected together, if desired. For example, the various interspinous spacers 10 could be coupled or connected together via a mechanical fastener, such as a screw, bolt, etc., or via a coating, connecting rod, suture, etc.

With particular reference to FIGS. 1-3A, the interspinous spacer 10 can include a body 14, an actuator system 16 and at least one deployable member 18. As will be discussed herein, the actuator system 16 can move the at least one deployable member 18 from a first, retracted position relative to the body 14 (FIG. 1) to a second, deployed position relative to the body 14 (FIG. 2). An insertion instrument 20 (FIG. 3A) can cooperate with the actuator system 16 to move the at least one deployable member 18 from the first, retracted position (e.g., FIG. 1) to the second, deployed position (e.g., FIG. 2) as will be discussed further herein.

In one example, with reference to FIGS. 3-6, the body 14 can be dynamic and can include a first slot 22, a second slot 24, a first throughbore 26, a second throughbore 28, and a third or central throughbore 30. The body 14 can also include a first or top surface 32, a second or bottom surface 34 and one or more coupling features 35. The body 14 can be composed of any suitable biocompatible material, such as a biocompatible metal, metal alloy, polymer or combinations thereof, and for example, can be composed of polyetheretherketone (PEEK), titanium, cobalt-chromium, etc. In addition, the body 14 could be composed of a resorbable material. Further, the body 14 can be coated with a biocompatible coating such as an antibiotic, bone growth enhancing material, or the like, to promote healing and bone integration.

The first slot 22 can be formed adjacent to the top surface 32, and the second slot 24 can be formed adjacent to the bottom surface 34. The first slot 22 can extend from a first side 36 towards a second side 38, and the second slot 24 can extend from the second side 38 to the first side 36. The first slot 22 and the second slot 24 can cooperate to generally form an S-shape, which can enable the body 14 to act as a tension spring.

In this regard, the first slot 22 and second slot 24 can allow the body 14 to flex slightly based on the movement of the adjacent spinous processes 12. Such flexion may allow a patient with the interspinous spacer 10 to move more naturally (i.e., more anatomically correct). It should be understood, however, that the body 14 can have any suitable resilient shape, such as a C-shape, E-shape, etc. In addition, it will be understood that the present teachings are not limited to a dynamic body 14.

With reference to FIGS. 3A-6, each of the first throughbore 26, the second throughbore 28 and the central throughbore 30 can extend from a third side 40 to a fourth side 42. Generally, the first throughbore 26 can be formed adjacent to the first side 36, and the second throughbore 28 can be formed adjacent to the second side 38. With reference to FIG. 3A, the first throughbore 26 can be formed at a height H1 relative to the bottom surface 34, and the second throughbore 28 can be formed at a height H2 relative to the bottom surface 34. In one example, the height H1 can be different from the height H2, and in a further example, the height H1 can be greater than the height H2. The first throughbore 26 and the second throughbore 28 can each receive a portion of the at least one deployable member 18 to couple the at least one deployable member 18 to the body 14, as will be discussed in greater detail herein.

The central throughbore 30 can generally be formed between the first throughbore 26 and the second throughbore 28, and can be substantially equally spaced from the first throughbore 26 and the second throughbore 28. The central throughbore 30 can slidably receive at least a portion of the actuator system 16 therethrough to enable the actuator system 16 to move the at least one deployable member 18 from the first, retracted position to the second, deployed position, as will be discussed in greater detail herein.

The top surface 32 can be opposite the bottom surface 34. The top surface 32 and the bottom surface 34 can be substantially flat, however, in one example, the top surface 32 and the bottom surface 34 can each have a slight taper T, or other suitable contour to facilitate the engagement of the top surface 32 and the bottom surface 34 with the adjacent spinous processes 12. In this example, the taper T can have the shape of a bicone, such that the taper T can direct the spinous process 12 to a center of the respective one of the top surface 32 or the bottom surface 34 (FIG. 10). Thus, the shape of the taper T can act to auto-center the spinous processes 12 on the interspinous spacer 10. In this regard, by including a taper T on the top surface 32 and the bottom surface 34, any force applied by the spinous processes 12 onto the interspinous spacer 10 can cause the respective spinous processes to follow the taper T, thereby aligning and centering the interspinous spacer 10 between the spinous processes 12.

Figure 4:
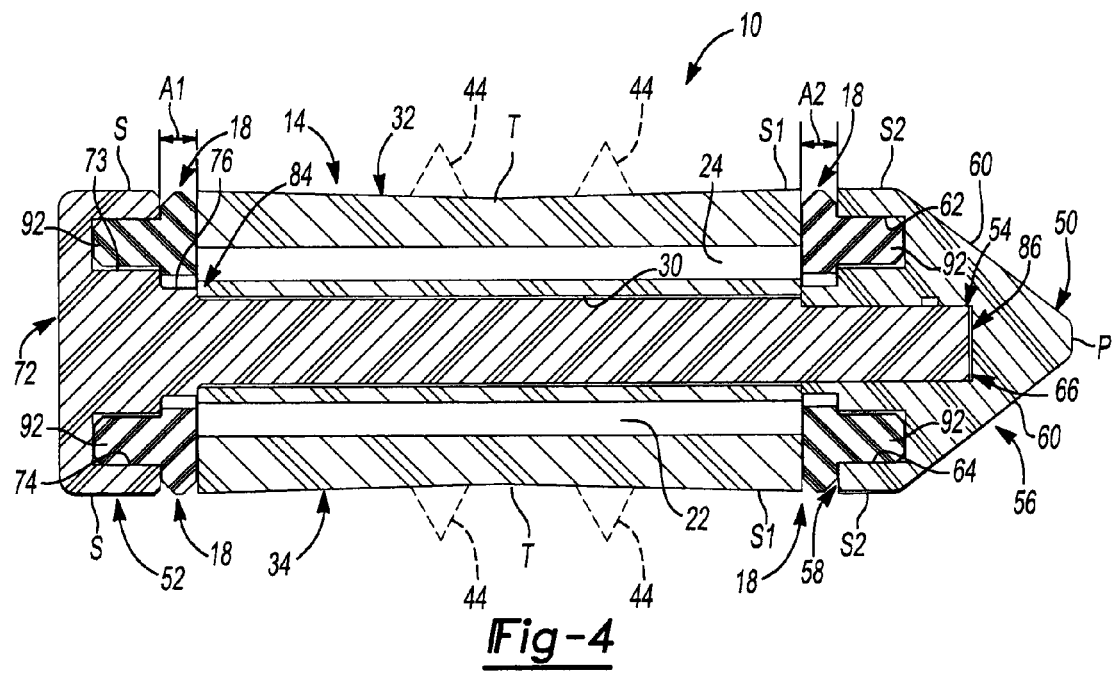
FIG. 4 is a schematic cross-sectional illustration of the interspinous spacer of FIG. 1, taken along line 4-4 of FIG. 1, illustrating an exemplary connector between a first cap and a second cap of the interspinous spacer.

In a further example, the top surface 32 and the bottom surface 34 can optionally include at least one tooth 44, which for the sake of clarity is only illustrated in FIG. 4. The at least one tooth 44 can engage, alter or bite into the spinous processes 12 to further secure the interspinous spacer 10 to the anatomy. The at least one tooth 44 can be positioned at any desired location on the top surface 32 and the bottom surface 34, and if desired, could be positioned on only one of the top surface 32 and the bottom surface 34. In addition, it should be noted that any other device could be employed to further secure the interspinous spacer 10 to the anatomy, such as a coating, adhesive, cable, screws, etc.

With reference to FIG. 3, the coupling features 35 can couple the body 14 to the insertion instrument 20. In one example, the coupling features 35 can include a first channel 35a and a second channel 35b. Each of the first channel 35a and the second channel 35b can be defined in the fourth side 42 of the body 14, and can be sized to receive at least a portion of the insertion instrument 20, as will be discussed in greater detail herein.

With reference to FIGS. 1-6, the actuator system 16 can cooperate with the insertion instrument 20 to move the at least one deployable member 18 from the first, retracted position to the second, deployed position. It should be understood that the use of an actuator system 16 may be optional, as the deployable members 18 could be biased to automatically deploy upon insertion into the anatomy. The actuator system 16 can include a first or driven cap 50, a second or driving cap 52 and a connector 54. The driven cap 50, the driving cap 52 and the connector 54 can be composed of suitable biocompatible materials, such as a biocompatible metal, metal alloy, polymer, or combination thereof. In one example, each of the driven cap 50, the driving cap 52 and the connector 54 can be composed of a metal or metal alloy, such as titanium. The driven cap 50 and the driving cap 52 can protect the at least one deployable member 18 when the at least one deployable member 18 is in the first, deployed position, as will be discussed in greater detail herein. The driven cap 50 can be coupled to the driving cap 52 via the connector 54.

With reference to FIGS. 3 and 3A, the driven cap 50 can include a first or distal end 56 (FIG. 3) and a second or proximal end 58 (FIG. 3A). As shown in FIG. 3A, the distal end 56 can include one or more sloped surfaces 60, which can meet at a point P. The sloped surfaces 60 can guide the interspinous spacer 10 into the anatomy. With reference to FIG. 3A, the proximal end 58 can include a first recess 62, a second recess 64 and a third or connector recess 66. In addition, if desired, the proximal end 58 can include one or more guides, which can direct the at least one deployable member 18 between the first, retracted position and the second, deployed position.

With reference to FIGS. 3 and 4, the first recess 62 can be positioned generally opposite the second recess 64, and each of the first recess 62 and the second recess 64 can be about equally spaced apart from the connector recess 66. The first recess 62 and the second recess 64 can each receive a portion of the at least one deployable member 18, to couple the at least one deployable member 18 to the driven cap 50.

With reference to FIG. 3, the connector recess 66 can couple the connector 54 to the driven cap 50. Generally, the connector recess 66 can include a flange 66a and a keyed portion 66b. The flange 66a can guide the connector 54 into engagement with the keyed portion 66b, and can assist in maintaining the connection between the connector 54 and the driven cap 50. The keyed portion 66b can enable the driven cap 50 to rotate with the driving cap 52. In one example, the keyed portion 66b can comprise a flat surface, however, the keyed portion 66b can have any desired shape, such as tongued, starred, notched, etc.

With reference to FIGS. 3 and 3A, the driving cap 52 can include a first or distal end 70 (FIG. 3A) and a second or proximal end 72 (FIG. 3). The distal end 70 can include a first recess 73, a second recess 74 and connector flange 76. In addition, if desired, the proximal end 58 can include one or more guides, which can direct the at least one deployable member 18 between the first, retracted position and the second, deployed position. The driving cap 52 can also include a viewing window, if desired, to allow the operator to view the deployment of the deployable members 18.

With continued reference to FIG. 3A, the first recess 73 can be positioned generally opposite the second recess 74, and each of the first recess 73 and the second recess 74 can be about equally spaced apart from the connector flange 76. The first recess 73 and the second recess 74 can each receive a portion of the at least one deployable member 18, to couple the at least one deployable member 18 to the driving cap 52.

The connector flange 76 can support the connector 54 as it extends from the driving cap 52. In one example, the connector 54 can be integrally formed with the driving cap 52, however, the connector 54 could be coupled to the driving cap 52 through any suitable technique, such as welding, adhesives, press-fitting, mechanical fasteners, etc. Thus, it should be understood that the connector 54 is not limited to being integrally formed with the driving cap 52.

With reference to FIG. 3, the proximal end 72 can be configured to mate with the insertion instrument 20. In one example, the proximal end 72 can include a coupling bore 78, a first groove 80 and a second groove 82. The coupling bore 78 can be threaded, and can receive a threaded fastening member to couple the interspinous spacer 10 to the insertion instrument 20, as will be discussed further herein. The first groove 80 can be defined opposite the second groove 82. The first groove 80 and the second groove 82 can receive a portion of the insertion instrument 20 to enable the driving cap 52 to be moved or rotated relative to the body 14 via the insertion instrument 20.

Figure 6:
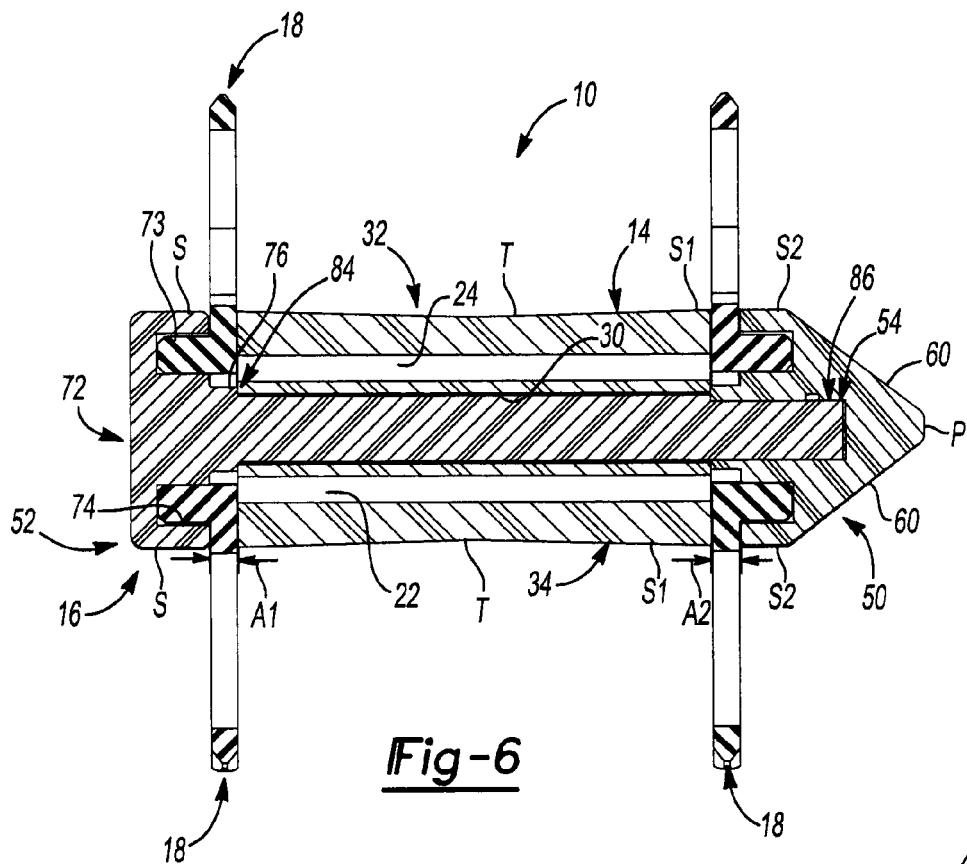
FIG. 6 is a schematic cross-sectional illustration of the interspinous spacer of FIG. 1, taken along line 6-6 of FIG. 2, illustrating a position of the at least one deployable member in the second, deployed position relative to a body of the interspinous spacer.

With reference to FIGS. 3, 4, and 6, the connector 54 can couple the driving cap 52 to the driven cap 50 through the body 14 (FIGS. 4 and 6). In this regard, the connector 54 can be substantially cylindrical and can be sized to be slidably received through the central throughbore 30 of the body 14 such that the connector 54 can rotate within and relative to the body 14. With reference to FIGS. 4 and 6, the connector 54 can include a first or proximal end 84 and a second or distal end 86. The proximal end 84 can be coupled to or formed with the driving cap 52, and can be surrounded by the connector flange 76.

The distal end 86 of the connector 54 can be coupled to the connector recess 66 of the driven cap 50. Generally, with reference to FIG. 3, the distal end 86 can include a keyed portion 86a, which can be shaped to match or cooperate with the keyed portion 66b of the connector recess 66 of the driven cap 50. The use of the keyed portions 66b, 86a can ensure that the driven cap 50 rotates with the driving cap 52. Thus, the connector 54 can serve to transfer torque from the driving cap 52 to the driven cap 50 so that the driven cap 50 can rotate substantially simultaneously with the driving cap 52. The substantially simultaneous rotation of the driving cap 52 and the driven cap 50 can enable the substantially simultaneous deployment of the at least one or more deployable members 18.

In this regard, with reference to FIG. 3A, the at least one deployable member 18 can include a first deployable member 18a, a second deployable member 18b, a third deployable member 18c and a fourth deployable member 18d. It will be understood that although the interspinous spacer 10 is described and illustrated herein as including four deployable members 18, any number of deployable members 18 from one to four could be employed with the interspinous spacer 10.

The deployable members 18 can be composed of any suitable biocompatible material, such as a biocompatible metal, metal alloy or polymer. In addition, the deployable members 18 can be coated, if desired, with a biocompatible material, such as an antibiotic, bone growth enhancing material, or the like, to promote healing and bone integration. In one example, the deployable members 18 can be composed of an elastic metal or metal alloy, such as titanium or nickel titanium. The use of an elastic biocompatible material can enable the deployable members 18 to be repeatably deformed. In this regard, as the deployable members 18 can be deformed as the deployable members 18 move from the first, retracted position to the second, deployed position, the use of an elastic biocompatible material can enable the deployable members 18 to be easily removed from the anatomy after implantation.

In this example, the first deployable member 18a and the second deployable member 18b can be coupled between the driving cap 52 and the body 14, while the third deployable member 18c and the fourth deployable member 18d can be coupled between the driven cap 50 and the body 14. Generally, the deployable members 18 can be sized such that the deployable members 18 are protected by the driven cap 50 and driving cap 52 when the deployable members 18 are in the first, retracted position. In other words, with reference to FIG. 4, a space or area A1 can be defined between the driving cap 52 and the body 14, and a space or area A2 can be defined between the driven cap 50 and the body 14. In the first, retracted position, the deployable members 18 can be folded so as to be below surfaces S of the driven cap 50, surfaces S1 of the body 14 and surfaces S2 of the driving cap 52, and thus, retained wholly within the areas A1, A2.

In the second, deployed position, with reference to FIG. 6, the deployable members 18 can be extended beyond the surfaces S of the driven cap 50, the surfaces S1 of the body 14 and the surfaces S2 of the driving cap 52. In the second, deployed position, the deployable members 18 can extend generally perpendicular to a longitudinal axis of the interspinous spacer 10. Generally, in the second, deployed position, at least two of the deployable members 18 can extend beyond the top surface 32 of the body 14, and at least two of the deployable members 18 can extend beyond the bottom surface 34 of the body 14. Thus, in the second, deployed position, the deployable members 18 can define a U-shaped channel, which can be positioned about the spinous processes 12 to retain the interspinous spacer 10 between the spinous processes 12. In addition, the deployable members 18, when in the second, deployed position can retain a bone graft, if desired. Note that in the second, deployed position, the areas A1, A2 are not modified, but rather, the areas A1, A2 remain constant in volume throughout the movement of the deployable members 18 between the first, retracted position and the second, deployed position. It should be noted that although the deployable members 18 are described and illustrated herein as substantially simultaneously moving between the first, retracted position and the second, deployed position, it will be understood that the deployable members 18 could move between the first, retracted position and the second, deployed position individually, in pairs, etc.

As each of the deployable members 18 can be substantially identical, the same reference numerals will be used to describe the same parts or features. In one example, with reference to FIG. 3A, the deployable members 18 can be generally V-shaped, however, the deployable members 18 can have any desired shape, such as U-shaped, C-shaped, etc. Each of the deployable members 18 can include a first end or tip 90, a second end or tip 92, a first arm 94 and a second arm 96.

Figure 5:
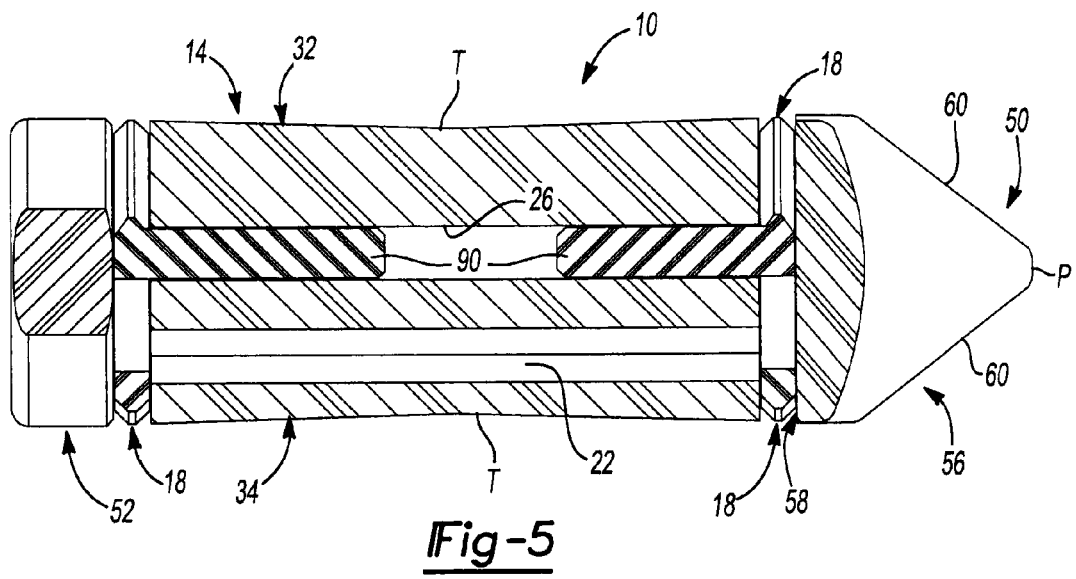
FIG. 5 is a schematic cross-sectional illustration of the interspinous spacer of FIG. 1, taken along line 5-5 of FIG. 1, illustrating an exemplary fixation location for at least one deployable member of the interspinous spacer.

With reference to FIG. 5, the first tip 90 can couple the deployable member 18 to a respective one of the first throughbore 26 or the second throughbore 28 of the body 14. Generally, the first tip 90 can define a first axis, and the deployable member 18 can pivot or rotate about the first axis. The first tip 90 can have a length, which can be greater than a length of the second tip 92 (FIG. 4), to provide stability for the movement or rotation of the deployable member relative to the body 14.

With reference to FIG. 4, the second tip 92 can couple the deployable member 18 to a respective one of the driven cap 50 or driving cap 52. The second tip 92 can define a second axis, and the deployable member 18 can pivot or rotate about the second axis. Note that the first axis is offset from the second axis. It should be understood, however, that the use of the first tip 90 and second tip 92 is merely exemplary, as any suitable technique could be used to rotatably couple the deployable member 18 to the body 14 and driven cap 50 or driving cap 52, such as magnetic coupling, etc.

With reference to FIGS. 2-3A, the first arm 94 can be arcuate, and can include a sloped exterior surface to facilitate the movement of the first arm 94 between the first, retracted position and the second, deployed position. The second arm 96 can be arcuate, and can have a sloped exterior surface. The first arm 94 and second arm 96 can meet in a point.

Figure 7:
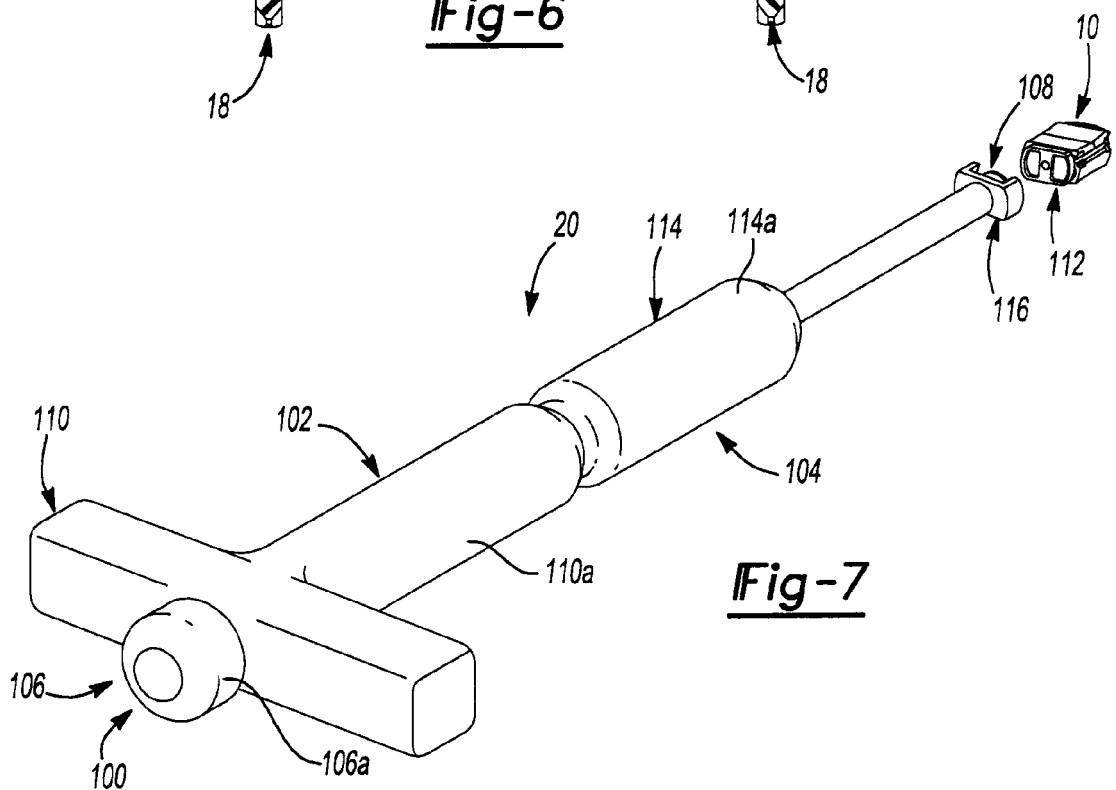
FIG. 7 is a schematic perspective illustration of the tool operatively associated with the interspinous spacer which can be used to insert the interspinous spacer of FIG. 1 into the anatomy.

With reference to FIGS. 3A, 7 and 8, the insertion instrument 20 can be coupled to the body 14 of the interspinous spacer 10 and the driving cap 52 to insert the interspinous spacer 10 into an anatomy, such as between adjacent spinous processes 12. With reference to FIG. 7, the insertion instrument 20 can include a fastening member 100, a deployment member 102 and a housing 104. The fastening member 100 can be received through the deployment member 102 and the housing 104 and can be rotatable relative to the deployment member 102 and the housing 104. The fastening member 100 can include a first or proximal end 106 and a second or distal end 108. The proximal end 106 can include a graspable portion 106a. The graspable portion 106a can enable a user to rotate the fastening member 100 to couple and uncouple the interspinous spacer 10 to the insertion instrument 20. With reference to FIG. 3A, the distal end 108 can include at least a threaded end 108a. The threaded end 108a can be configured to threadably engage the coupling bore 78 (FIG. 3) of the driving cap 52 upon the rotation of the graspable portion 106a to couple the interspinous spacer 10 to the insertion instrument 20.

With reference back to FIG. 7, the deployment member 102 can be received through the housing 104 and can be rotatable relative to the fastening member 100 and the housing 104. The deployment member 102 can include a first or proximal end 110 and a second or distal end 112. The proximal end 110 can include a graspable portion 110a. The graspable portion 110a can enable a user to rotate the deployment member 102 to move the deployable members 18 between the first, retracted position and the second, deployed position.

In this regard, with reference to FIG. 3A, the distal end 112 can include a first pin 112a spaced apart from a second pin 112b. The first pin 112a and the second pin 112b can engage a respective one of the first groove 80 and second groove 82 (FIG. 3) of the driving cap 52 when the interspinous spacer 10 is coupled to the insertion instrument 20. The rotation of the graspable portion 110a can rotate the first pin 112a and the second pin 112b, which in turn can rotate the driving cap 52. The rotation of the driving cap 52 can move the deployable members 18 between the first, retracted position and the second, deployed position.

With reference to FIG. 7, the housing 104 can receive the fastening member 100 and the deployment member 102 therethrough, and can be configured to enable the fastening member 100 and the deployment member 102 to rotate relative to the housing 104. The housing 104 can include a first or proximal end 114 and a second or distal end 116. The proximal end 114 can include a graspable portion 114a. The graspable portion 114a can provide a grip to facilitate the rotation of the fastening member 100 and the deployment member 102 relative to the housing 104. With reference to FIG. 3A, the distal end 116 can include a first pin 116a spaced apart from a second pin 116b. The first pin 116a and the second pin 116b can engage a respective one of the coupling features 35 (FIG. 3) of the body 14 when the interspinous spacer 10 is coupled to the insertion instrument 20. The first pin 116a and the second pin 116b can prevent the body 14 from rotating with the rotation of the driving cap 52 and driven cap 50 to allow the movement of the deployable members 18 between the first, retracted position and the second, deployed position.

In one example, with reference to FIGS. 3 and 3A, in order to assemble the interspinous spacer 10, the connector 54 can be coupled to the driving cap 52. Then, the first tip 90 of the first deployable member 18a and the second deployable member 18b can be coupled to a respective one of the first throughbore 26 and the second throughbore 28 of the body 14 (FIG. 3A). The first tip 90 of the third deployable member 18c and the fourth deployable member 18d can also be coupled to a respective one of the first throughbore 26 and the second throughbore 28 of the body 14 (FIG. 3A).

Then, the connector 54 can be slidably inserted through the central throughbore 30 of the body 14. The movement of the connector 54 through the central throughbore 30 can align the second tip 92 of the first deployable member 18a and the second deployable member 18b with the first recess 73 and second recess 74 of the driving cap 52. The connector 54 can be advanced through the central throughbore 30 so that the second tip 92 of the first deployable member 18a and the second deployable member 18b can be coupled to a respective one of the first recess 73 and second recess 74 of the driving cap 52 (FIG. 4). Next, the driven cap 50 can be coupled to the distal end 86 of the connector 54, and the second tip 92 of the third deployable member 18c and the fourth deployable member 18d can be coupled to a respective one of the first recess 62 and second recess 64 of the driven cap 50 (FIG. 4).

With the interspinous spacer 10 assembled, with reference to FIGS. 8-11, in order to insert the interspinous spacer 10 into an anatomy, such as between adjacent spinous processes 12, the anatomy can be prepared to receive in the interspinous spacer 10. In this regard, surgical access can be made to an area A3 adjacent to the spinous processes 12 (FIG. 8). The specific surgical access approaches are beyond the scope of the present application, but for example, surgical access can be obtained via a minimally invasive surgical procedure or a posterior unilateral open procedure. In the case of a minimally invasive surgical procedure, surgical access to the lumbar spine can be made using the AccuVision™ Minimally Invasive Spinal Exposure System, commercially available from Biomet, Inc. of Warsaw, Ind., for example.

In the example of a minimally invasive surgical procedure, with reference to FIG. 8, a catheter or dilator 130 can be positioned next to the spinous processes 12. With the interspinous spacer 10 positioned in the first, retracted position, the insertion instrument 20 can be coupled to the fourth side 42 of the interspinous spacer 10. In this regard, the fastening member 100 (FIG. 7) can be coupled to the coupling bore 78 (FIG. 3) of the driving cap 52 to couple the interspinous spacer 10 to the insertion instrument 20. With the interspinous spacer 10 coupled to the insertion instrument 20, the first pin 112a and the second pin 112b can be coupled to the first groove 80 and second groove 82 of the driving cap 52, and the first pin 116a and the second pin 116b can be coupled to the coupling features 35 of the body 14 (FIG. 8).

With the interspinous spacer 10 coupled to the insertion instrument 20, the interspinous spacer 10 and the insertion instrument 20 can be inserted through the dilator 130 adjacent to the area A3. Then, the interspinous spacer 10 can be advanced from the dilator 130 into an area A4 between the adjacent spinous processes 12 as shown in FIG. 9. With the interspinous spacer 10 positioned between the adjacent spinous processes 12, with reference to FIG. 10, the deployment member 102 can be rotated clockwise to rotate the driving cap 52 and the driven cap 50. The substantially simultaneous rotation of the driving cap 52 and the driven cap 50 can substantially simultaneously move all of the deployable members 18 from the first, retracted position to the second, deployed position, as shown in FIGS. 10 and 11.

Generally, as the driving cap 52 and the driven cap 50 are rotated, the deployable members 18 are deformed. Once the maximum deformation of each of the deployable members 18 has been reached, such that each of the deployable members 18 have been moved to the second, deployed position, the deployable members 18 can return to their original shape. In this regard, as the deployable members 18 are composed of an elastically deformable material, the deployable members 18 can return to their original shape while remaining in the second, deployed position.

With the deployable members 18 in the second, deployed position, as shown in FIGS. 10 and 11, the interspinous spacer 10 can be properly positioned within the anatomy. The deployable members 18 can retain the interspinous spacer 10 between the adjacent spinous processes 12. Further, if the at least one tooth 44 is included on either or both of the top surface 32 and bottom surface 34, then the at least one tooth 44 can bite into or alter the spinous processes 12 to further secure the interspinous spacer 10 to the anatomy. In addition, in the case of the use of multiple interspinous spacers 10 deployed in an anatomy, the interspinous spacers 10 can be coupled or connected together to provide additional stability. In one example, at least one or more of the deployable members 18 associated with each of the interspinous spacers 10 can be coupled together via a fixation device, such as a mechanical fastener, suture, coating, adhesive, etc.

Figure 12:
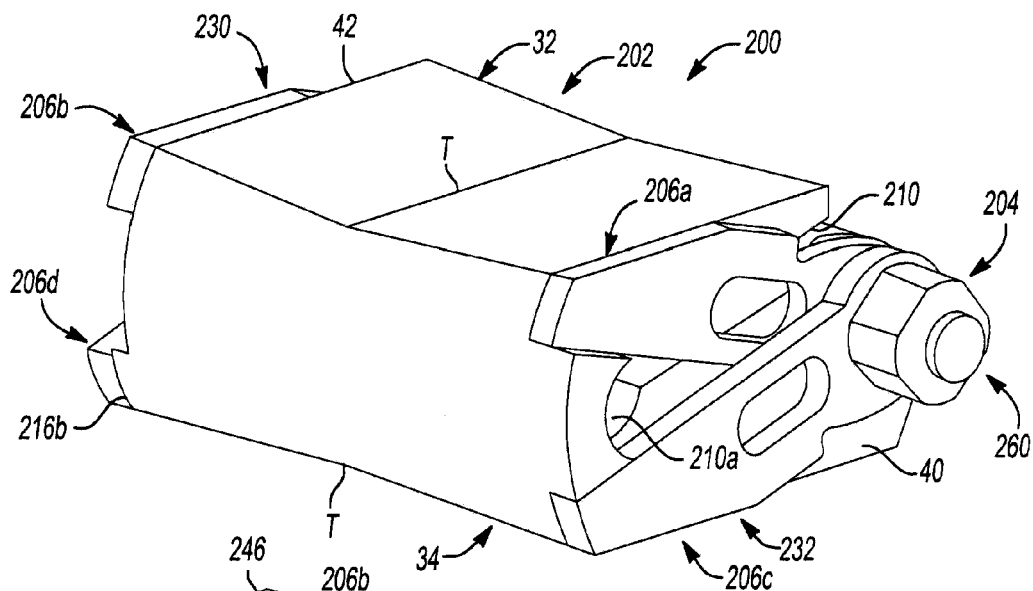
FIG. 12 is a schematic illustration of another exemplary interspinous spacer according to one of various teachings in a first, retracted state.
Figure 13:
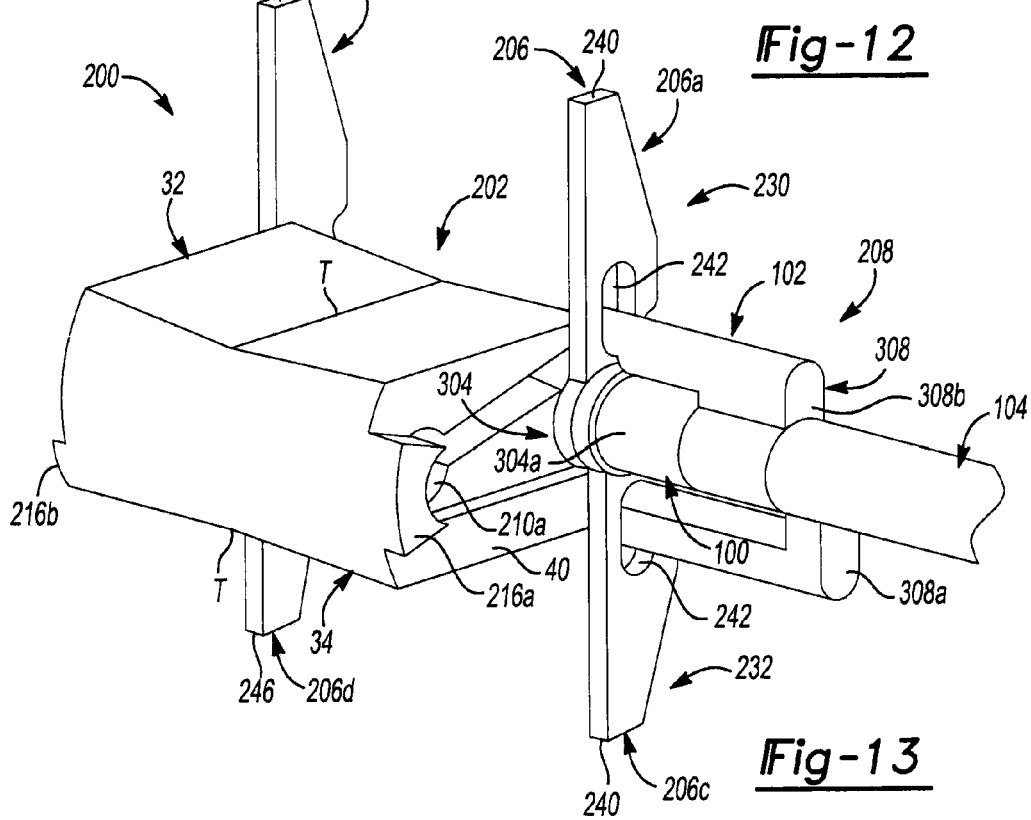
FIG. 13 is a schematic environmental illustration of the interspinous spacer of FIG. 12 in a second, deployed state operatively illustrated with a tool for moving the interspinous spacer between the first, retracted state and the second, deployed state.
Figure 14:
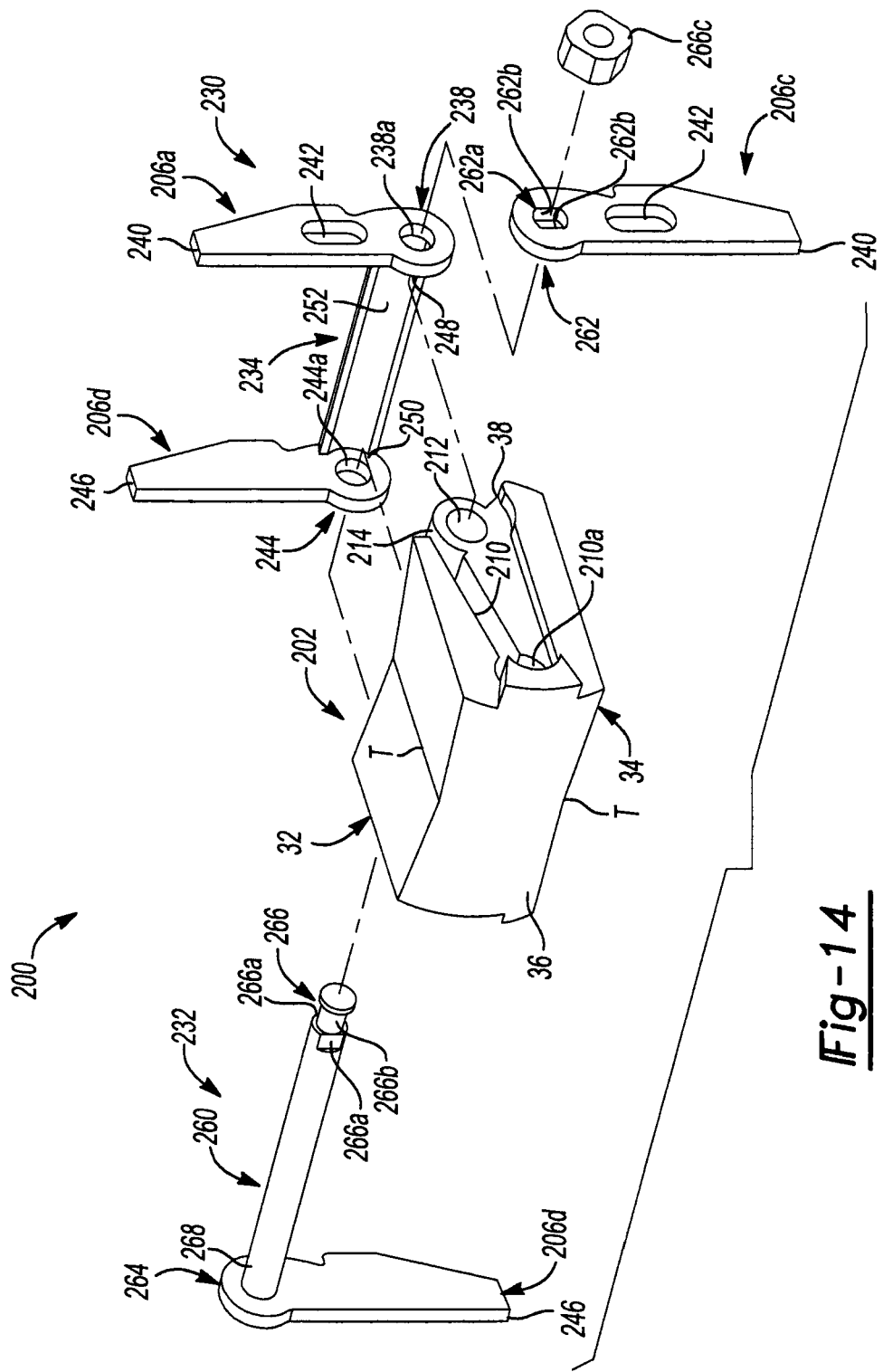
FIG. 14 is an exploded schematic illustration of the interspinous spacer of FIG. 12.

With reference now to FIGS. 12-14, in one example, an interspinous spacer 200 can be employed to repair a damage portion of an anatomy. As the interspinous spacer 200 can be similar to the interspinous spacer 10 described with reference to FIGS. 1-11, only the differences between the interspinous spacer 10 and the interspinous spacer 200 will be discussed in great detail herein, and the same reference numerals will be used to denote the same or similar components.

With continued reference to FIGS. 12-14, the interspinous spacer 200 can include a body 202 and an actuator system 204. The actuator system 204 can include at least one deployable member 206. As will be discussed herein, the actuator system 204 can move the at least one deployable member 206 from a first, retracted position relative to the body 202 (e.g., FIG. 12) to a second, deployed position relative to the body 202 (e.g., FIG. 13). An insertion instrument 208 (FIG. 13) can cooperate with the actuator system 204 to move the at least one deployable member 206 from the first, retracted position (FIG. 12) to the second, deployed position (FIG. 13) as will be discussed further herein.

In one example, the body 202 can include a first slot 210, a first throughbore 212, an articulating or bearing surface 214 (FIG. 14) and one or more guides 216. The body 202 can also include the first or top surface 32 and the second or bottom surface 34. The body 202 can be composed of any suitable biocompatible material, such as a biocompatible metal, metal alloy, polymer or combinations thereof, and for example, can be composed of polyetheretherketone (PEEK).

The first slot 210 can be formed adjacent to the top surface 32, and can be angled or have a negative slope such that the first slot 210 terminates substantially adjacent to the bottom surface 34. The first slot 210 can also include an arcuate or annular region 210a. The shape of the first slot 210 can cause the body 202 to be formed into a substantially U-shape, which can enable the body 202 to act as a tension spring. The first slot 210 can extend from the second side 38 towards the first side 36.

With continued reference to FIGS. 12-14, each of the first throughbore 212 and the bearing surface 214 can extend from the third side 40 to the fourth side 42. Generally, the first throughbore 212 can be formed adjacent to the first side 36, and can be formed substantially opposite the annular region 210a of the first slot 210. The first throughbore 212 receive a portion of the at least one deployable member 206 to couple the at least one deployable member 206 to the body 202, as will be discussed in greater detail herein.

The bearing surface 214 can be formed about the first throughbore 212 such that the bearing surface 214 can substantially circumscribe the first throughbore 212. Thus, bearing surface 214 can be generally cylindrical, and can have an arcuate surface that can engage at least a portion of the actuator system 16 thereon. It will be understood, however, that the bearing surface 214 can have any desired surface suitable for the rotation of the actuator system 204 thereon, as will be discussed in greater detail herein.

The guides 216 can support the at least one deployable member 208. Generally, the guides 216 can include a first guide 216a and a second guide 216b. In one example, the first guide 216a can extend from the third side 40 and the second guide 216b can extend from the fourth side 42. The first guide 216a can generally be shaped to support at least a portion of the at least one deployable member 206 when the at least one deployable member 206 is in the first, retracted position, as will be discussed herein. The second guide 216b can extend from the body 202 to contact the at least one deployable member 208, as will be discussed in greater detail herein.

With continued reference to FIGS. 12-14, the actuator system 204 can cooperate with the insertion instrument 208 to move the at least one deployable member 206 from the first, retracted position (FIG. 12) to the second, deployed position (FIG. 13). The actuator system 204 can include a first or upper deployable system 230 and a second or lower deployable system 232. Each of the upper deployable system 230 and the lower deployable system 232 can include at least deployable member 206.

In this regard, the upper deployable system 230 can include a first driving deployable member 206a, a second driven deployable member 206b and a connecting member 234 (FIG. 14). In one example, the first driving deployable member 206a, the second driven deployable member 206b and the connecting member 234 can be integrally formed from a suitable biocompatible material, such as a biocompatible metal, metal alloy or polymer. It should be understood, however, that the first driving deployable member 206a, the second driven deployable member 206b and the connecting member 234 could be formed as discrete components and assembled through any suitable technique, such as welding, adhesives, fasteners, etc. The first driving deployable member 206a and the second driven deployable member 206b can have a generally sharp exterior or anterior surface, which can facilitate the movement of the first driving deployable member 206a and the second driven deployable member 206b from the first, retracted position to the second, deployed position. Generally, in the second, deployed position, the first driving deployable member 206a and the second driven deployable member 206b can form a U-shaped channel, which can be receive a respective one of the spinous processes 12.

As best illustrated in FIG. 14, the first driving deployable member 206a can include a first or proximal end 238, a second or distal end 240 and a slot 242 formed between the proximal end 238 and the distal end 240. The proximal end 238 can define a bore 238a, which can receive at least a portion of the lower deployable system 232 therethrough to enable the upper deployable system 230 to move or rotate with the lower deployable system 232. The slot 242 can be sized to receive at least a portion of the insertion instrument 208 therethrough (FIG. 13). As will be discussed, the insertion instrument 208 can move the first driving deployable member 206a relative to the body 202 to move the upper deployable system 230 between the first, retracted position and the second, deployed position.

With continued reference to FIG. 14, the second driven deployable member 206b can include a first or proximal end 244 and a second or distal end 246. The proximal end 244 can define a bore 244a, which can receive at least a portion of the lower deployable system 232 therethrough to enable the upper deployable system 230 to move or rotate with the lower deployable system 232. Note that although the second driven deployable member 206b is not illustrated herein as including a slot, the second driven deployable member 206b could include a slot if desired. For example, the second driven deployable member 206b could include a slot to reduce manufacturing time or allow for interchangeable parts.

The connecting member 234 can couple the first driving deployable member 206a to the second driven deployable member 206b. The connecting member 234 can include a first end 248, a second end 250 and a articulating or bearing surface 252. In one example, the first end 248 can be coupled to the first driving deployable member 206a, and the second end 250 can be coupled to the second driven deployable member 206b. The bearing surface 252 can generally extend from the first end 248 to the second end 250. The bearing surface 252 can be sized and shaped to correspond to the bearing surface 214 of the body 202 so that the upper deployable system 230 can rotate relative to the body 202 on the bearing surface 214.

With continued reference to FIGS. 12-14, the lower deployable system 232 can include a third driving deployable member 206c, a fourth driven deployable member 206d and a connecting member 260. In one example, the third driving deployable member 206c, the fourth driven deployable member 206d and the connecting member 260 can be separately formed from a suitable biocompatible material, such as a biocompatible metal, metal alloy or polymer, and assembled into the lower deployable system 232 via a suitable manufacturing technique, such as welding, press-fitting, adhesives, fasteners, etc. It should be understood, however, that one or more of the first driving deployable member 206a, the second driven deployable member 206b and the connecting member 234 could be integrally formed, if desired. In one example, the fourth driven deployable member 206d and the connecting member 260 can be integrally formed, and the third driving deployable member 206c can be press-fit onto an end of the connecting member 260.

The third driving deployable member 206c and the fourth driven deployable member 206d can have a generally sharp exterior or anterior surface, which can facilitate the movement of the third driving deployable member 206c and the fourth driven deployable member 206d from the first, retracted position to the second, deployed position. Generally, in the second, deployed position, the third driving deployable member 206c and the fourth driven deployable member 206d can form a U-shaped channel, which can receive a respective one of the spinous processes 12 (FIG. 13).

As the third driving deployable member 206c can be similar to the first driving deployable member 206a described with reference to FIGS. 12-14, only the differences between the first driving deployable member 206a and the third driving deployable member 206c will be discussed in great detail herein, and the same reference numerals will be used to denote the same or similar components.

The third driving deployable member 206c can include a first or proximal end 262, the distal end 240 and the slot 242 formed between the proximal end 262 and the distal end 240. The proximal end 262 can define a bore 262a, which can couple the third driving deployable member 206c to the connecting member 260. In one example, the bore 262a can include one or more coupling surfaces 262b, which can prevent the third driving deployable member 206c from rotating relative to the connecting member 260. In this example, the coupling surfaces 262b can be flat or planar, and optionally, could be keyed.

As the fourth driven deployable member 206d can be similar to the second driven deployable member 206b described with reference to FIGS. 12-14, only the differences between the fourth driven deployable member 206d and the second driven deployable member 206b will be discussed in great detail herein, and the same reference numerals will be used to denote the same or similar components.

As best illustrated in FIG. 14, the fourth driven deployable member 206d can include a first or proximal end 264 and the distal end 246. The proximal end 264 can be coupled to the connecting member 260. In this example, the proximal end 264 can be integrally formed with the connecting member 260 so that the fourth driven deployable member 206d can rotate with the connecting member 260.

The connecting member 260 can couple the third driving deployable member 206c to the fourth driven deployable member 206d. In one example, the connecting member 260 can be cylindrical. The connecting member 260 can be received through the first throughbore 212 of the body 202. Generally, the connecting member 260 can be sized to be rotatable within the first throughbore 212 to enable the deployable members 206 to move or rotate from the first, retracted position to the second, deployed position, as will be discussed further herein.

The connecting member 260 can include a first end 266 and a second end 268. In one example, the first end 266 can be coupled to the third driving deployable member 206c. The first end 266 can include a one or more coupling surfaces 266a, a post 266b and an engagement member 266c. In one example, the coupling surfaces 266a can be shaped to mate with the coupling surfaces 262b of the third driving deployable member 206c to fixedly couple the third driving deployable member 206c to the connecting member 260.

In this example, the coupling surfaces 262b, 266a are flat or planar, however, it should be understood that the coupling surfaces 262b, 266a can have any suitable mating shape, such as keyed, notched, etc. Further, although the third driving deployable member 206c is described and illustrated herein as being press-fit to the connecting member 260, it should be understood that the third driving deployable member 206c can be coupled to the connecting member 260 through any suitable technique, such as welding, adhesives, fasteners, etc.

The post 266b can be formed at a proximal-most end 266d of the connecting member 260. Generally, the post 266b can extend beyond the body 202 when the lower deployable system 232 is coupled to the body 202. The post 266b can include a flange or lip, if desired, to retain the engagement member 266c on the post 266b.

The engagement member 266c can provide a point of attachment for the insertion instrument 208. In addition, the engagement member 266c can also assist in retaining the third driving deployable member 206c on the connecting member 260. In one example, the engagement member 266c can comprise a nut fixedly coupled to the post 266b, however, the engagement member 266c can comprise any suitable mechanism, such as a wing-nut, lock washer, etc. The second end 268 can be coupled to or integrally formed with the fourth driven deployable member 206d.

With reference to FIG. 13, the insertion instrument 208 can be coupled to the actuator system 204 of the interspinous spacer 200 to insert the interspinous spacer 200 into an anatomy, such as between adjacent spinous processes 12. As only the distal end of the insertion instrument 208 is substantially different from the insertion instrument 20 described with regard to FIGS. 1-11, only the distal end of the insertion instrument 208 will be discussed and illustrated in detail herein.

The insertion instrument 208 can include the fastening member 100, a deployment member 102 and the housing 104. The fastening member 100 can include the proximal end 106 and a second or distal end 304. The distal end 304 can be sized to engage the engagement member 266c of the connecting member 260 to couple the insertion instrument 208 to the interspinous spacer 200. In one example, if the engagement member 266c is a nut, then the distal end 304 can include a socket head 304a. The socket head 304a can hold the connecting member 260 fixed relative to the body 202 to enable the deployment member 102 to move or rotate the deployable members 206 between the first, retracted position and the second, deployed position.

The deployment member 102 can include the proximal end 110 and a second or distal end 308. The distal end 308 can include a first arm 308a and a second arm 308b. The first arm 308a can be spaced apart from a second arm 308b. The first arm 308a and the second first arm 308a can engage the respective slot 242 of the first driving deployable member 206a and the third driving deployable member 206c when the interspinous spacer 200 is coupled to the insertion instrument 208. The rotation of the deployment member 102 can rotate the first arm 308a and the second arm 308b, which in turn can rotate the second driven deployable member 206b and the fourth driven deployable member 206d to move the deployable members 206 between the first, retracted position and the second, deployed position.

In one example, with reference to FIGS. 12-14, in order to assemble the interspinous spacer 200, the connecting member 260 can be inserted through the first throughbore 212, so that the connecting member 260 is received through the bores 238a of the first driving deployable member 206a and the second driven deployable member 206b. With the upper deployable system 230 coupled to the body 202, the third driving deployable member 206c can be coupled to the coupling surfaces 266a of the connecting member 260. Then, the engagement member 266c can be secured to the post 266b.

With the interspinous spacer 200 assembled, with reference to FIGS. 12-14, in order to insert the interspinous spacer 200 into an anatomy, such as between adjacent spinous processes 12, the anatomy can be prepared to receive in the interspinous spacer 200. As the insertion of the interspinous spacer 200 can be similar to the insertion of the interspinous spacer 10, only the differences in the insertion of the interspinous spacer 10 and the interspinous spacer 200 will be discussed in great detail herein, and the same reference numerals will be used to denote the same or similar components. With the interspinous spacer 200 positioned in the first, retracted position, the insertion instrument 208 can be coupled to the fourth side 42 of the interspinous spacer 10. In this regard, the fastening member 100 can be coupled to the engagement member 266c of the actuator system 204 to couple the interspinous spacer 200 to the insertion instrument 208. With the interspinous spacer 200 coupled to the insertion instrument 208 the first arm 308a and the second arm 308b can be coupled to the slots 242 of the first driving deployable member 206a and the third driving deployable member 206c (FIG. 11).

Once the interspinous spacer 200 is positioned between the spinous processes 12, the deployment member 102 can be rotated clockwise to rotate the deployable members 206 from the first, retracted position to the second, deployed position. In this regard, the substantially simultaneous rotation of the first driving deployable member 206a and the third driving deployable member 206c can substantially simultaneously move all of the deployable members 206 from the first, retracted position (FIG. 12) to the second, deployed position (FIG. 13).

Accordingly, the interspinous spacer 10, 200 can be used to repair damaged tissue in the anatomy, such as in the case of spinal stenosis via insertion of the interspinous spacer 10, 200 between adjacent spinous processes 12. The shape of the body 14, 202 can enable the interspinous spacer 10, 200 to act as a tension spring, which can assist in restoring the motion of the damaged tissue. Further, the taper T of the top surface 32 and bottom surface 34 can allow the interspinous spacer 10, 200 to automatically center under loads or forces applied by the spinous processes 12. In addition, with reference to the interspinous spacer 10, since the deployable members 18 are elastically deformable, the interspinous spacer 10 can be easily removed from the anatomy after implantation, if desired.

Figure 15:
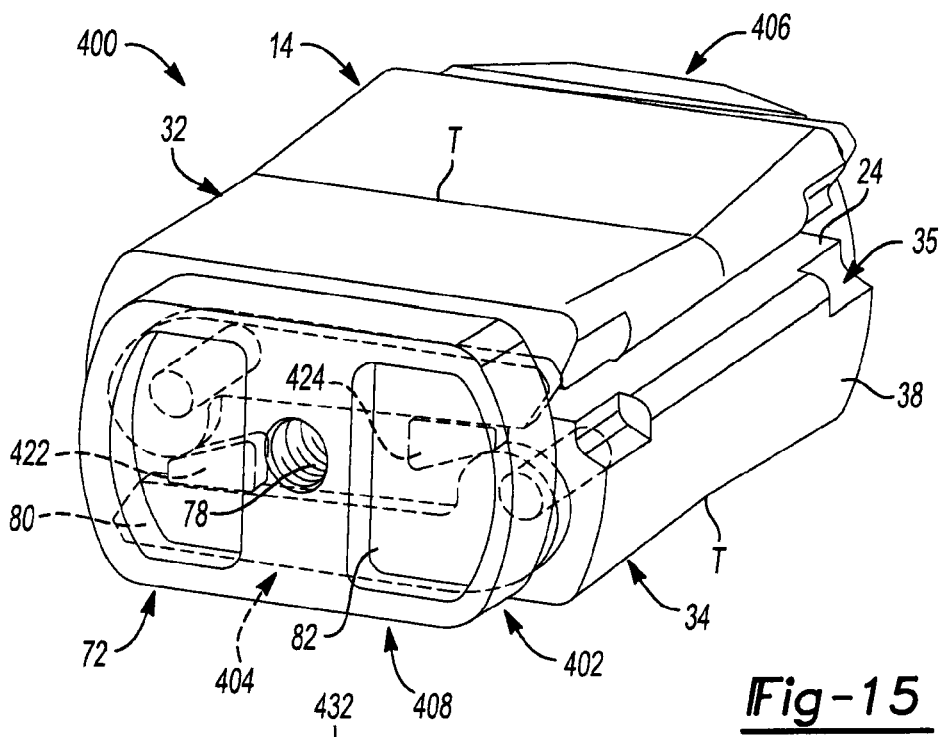
FIG. 15 is a schematic illustration of another exemplary interspinous spacer according to one of various teachings in a first, retracted state.
Figure 16:
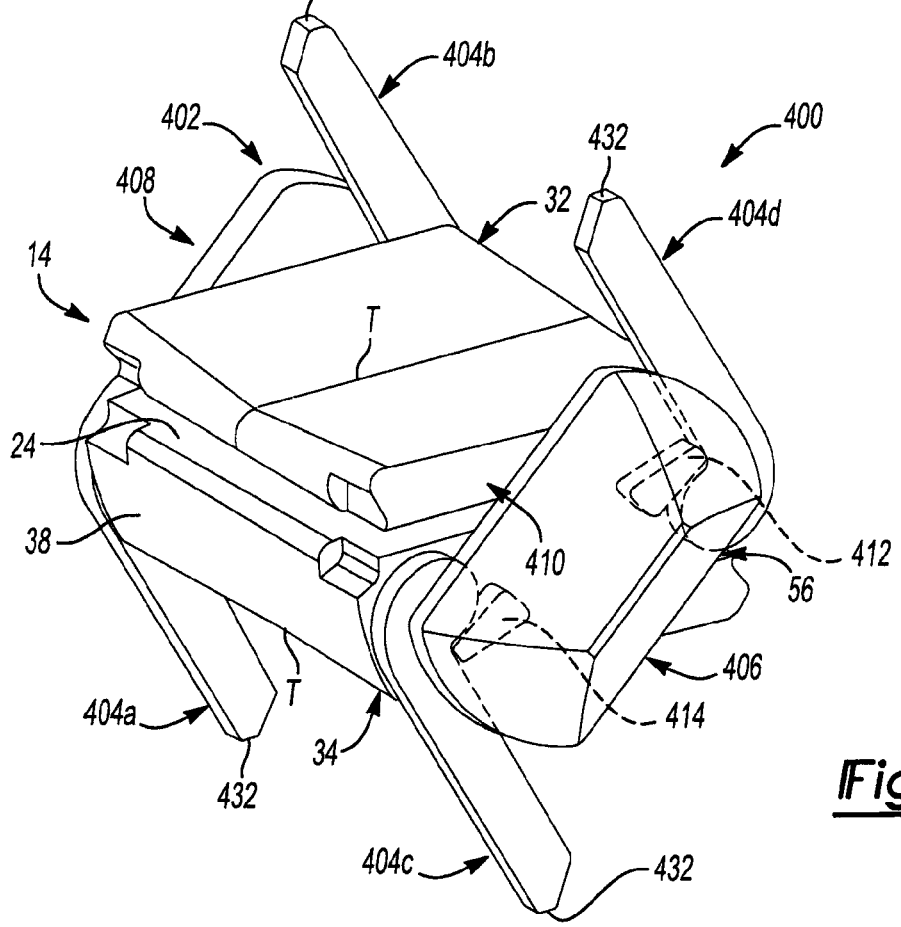
FIG. 16 is a schematic environmental illustration of the interspinous spacer of FIG. 15 in a second, deployed state.
Figure 17:
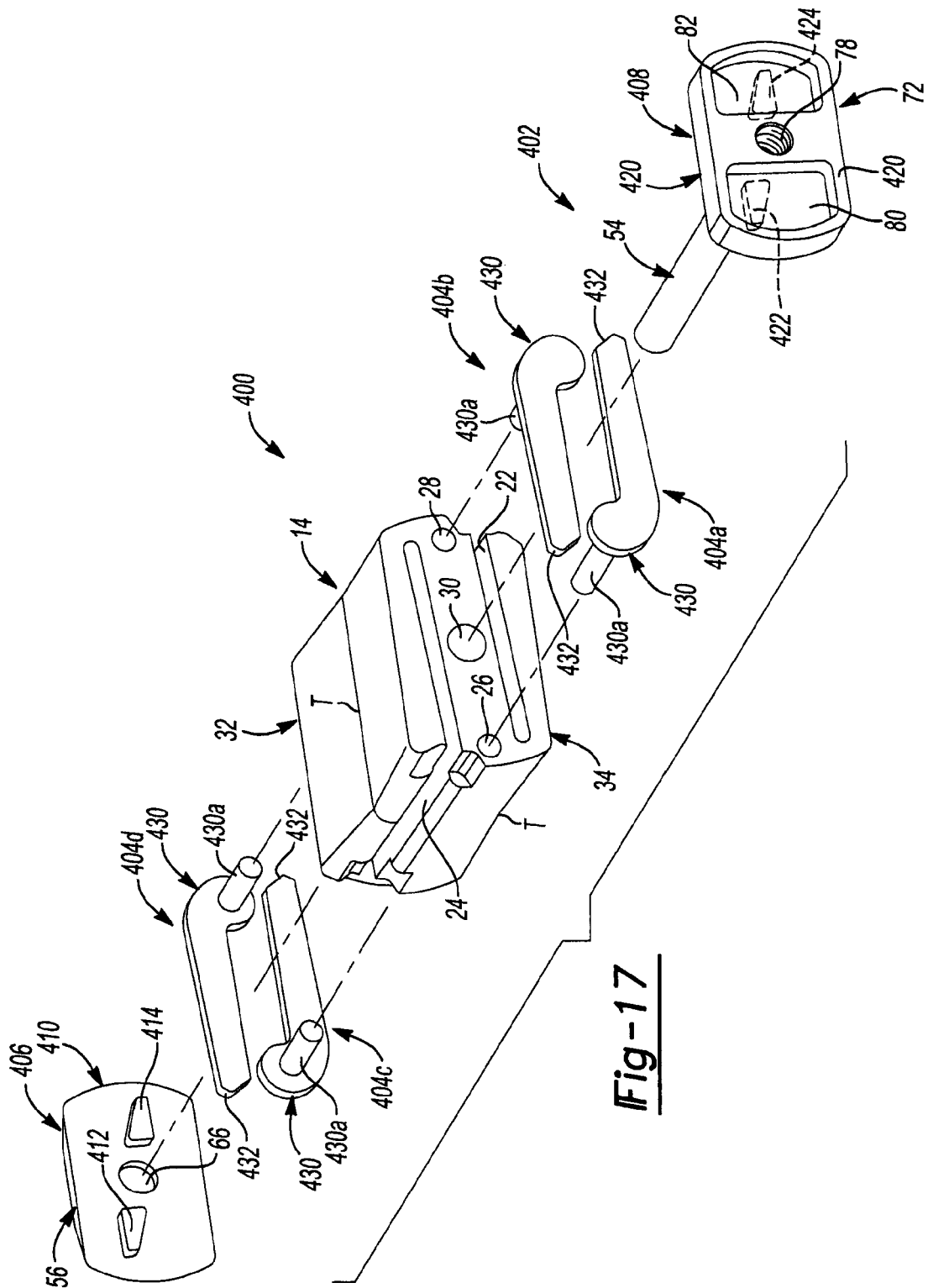
FIG. 17 is an exploded schematic illustration of the interspinous spacer of FIG. 15.

In another of various examples, with reference to FIGS. 15-17, an interspinous spacer 400 can be employed to repair a damage portion of an anatomy. As the interspinous spacer 400 can be similar to the interspinous spacer 10 described with reference to FIGS. 1-11, only the differences between the interspinous spacer 10 and the interspinous spacer 400 will be discussed in great detail herein, and the same reference numerals will be used to denote the same or similar components. In this example, the interspinous spacer 400 can include the body 14, an actuator system 402 and at least one deployable member 404. The actuator system 402 can cooperate with the insertion instrument 20 to move the at least one deployable member 404 from the first, retracted position (e.g., FIG. 15) to the second, deployed position (e.g., FIG. 16).

The actuator system 402 can include a first or driven cap 406, a second or driving cap 408 and the connector 54 (FIG. 17). The driven cap 406 can include the distal end 56 (FIG. 16) and a second or proximal end 410. With reference to FIG. 17, the proximal end 410 can include a first driving tip 412, a second driving tip 414 and the connector recess 66. The first driving tip 412 can be positioned generally opposite the second driving tip 414, and each of the first driving tip 412 and the second driving tip 414 can be about equally spaced apart from the connector recess 66. The first driving tip 412 and the second driving tip 414 can drive the at least one deployable member 404 between the first, retracted position and the second, deployed position.

With reference to FIG. 17, the driving cap 408 can include a first or distal end 420 and the proximal end 72. The distal end 420 can include a first driving tip 422, a second driving tip 424 and the connector flange 76. The first driving tip 422 can be positioned generally opposite the second driving tip 424, and each of the first driving tip 422 and the second driving tip 424 can be about equally spaced apart from the connector flange 76. The first driving tip 422 and the second driving tip 424 can move or rotate the at least one deployable member 404 between the first, retracted position and the second, deployed position.

In this example, with reference to FIGS. 16 and 17, the at least one deployable member 404 can include a first deployable member 404a, a second deployable member 404b, a third deployable member 404c and a fourth deployable member 404d. With reference to FIG. 17, the deployable members 404 can be substantially L-shaped, and each of the deployable members 404 can include a first or proximal end 430 and a second or distal end 432. The proximal end 430 can include a tip 430a, which can couple the deployable member 404 to a respective one of the first throughbore 26 or second throughbore 28 of the body 14. The distal end 432 can be coupled to or contacted by a respective one of the driving tips 412, 414, 422, 424 to move or rotate the at least one deployable member 404 between the first, retracted position (FIG. 15) and the second, deployed position (FIG. 16).

In this regard, with the interspinous spacer 400 assembled, the insertion instrument 20 can be used to rotate the driving cap 408. The rotation of the driving cap 408 can substantially simultaneously rotate the driven cap 406. The rotation of the driving cap 408 and the driven cap 406 can cause the respective driving tips 412, 414, 422, 424 to be coupled to or contact to all of the deployable members 404. The contact between the driving tips 412, 414, 422, 424 and the deployable members 404 can move the deployable members 404 between the first, retracted position (FIG. 15) and the second, deployed position (FIG. 16).

With reference to FIGS. 18-20, in another of various examples, an interspinous spacer 500 can include a body 502, an actuator system 504 and at least one deployable member 506. As the interspinous spacer 500 can be similar to the interspinous spacer 10 described with reference to FIGS. 1-11, only the differences between the interspinous spacer 10 and the interspinous spacer 500 will be discussed in great detail herein, and the same reference numerals will be used to denote the same or similar components. In this example, the at least one deployable member 506 comprises four deployable members 506a, 506b, 506c, 506d which will generally be referred to with the reference numeral 506. The actuator system 504 can cooperate with a suitable instrument to move the deployable members 506 from a first, retracted position (e.g., FIGS. 18, 18A, 20) to a second, deployed position (e.g., FIG. 19).

In one example, the body 502 can comprise a generally S-shaped body. The body 502 can be composed of any suitable biocompatible material, such as a biocompatible metal, metal alloy, polymer or combinations thereof, and for example, can be composed of polyetheretherketone (PEEK) or titanium. The body 502 can include a first or proximal end 510 and a second or distal end 512. Each of the proximal end 510 and the distal end 512 can define a throughbore 514. The throughbores 514 can extend in a direction generally transverse to a longitudinal axis L, and in one example, the throughbores 514 can extend in a direction generally perpendicular to the longitudinal axis L. The throughbores 514 can each receive a portion of the actuator system 504.

In this regard, the actuator system 504 can comprise at least one connecting arm 520, and in this example, can comprise two connecting arms 520a, 520b. A respective one of the connecting arms 520 can be received through a respective one of the throughbores 514. The connecting arms 520 can rotatably couple the deployable members 504 to the body 502, and each of the connecting arms 520 can have a first end 522 and a second end 524. Each of the first ends 522 and the second ends 524 can include grooves, channels, keyed portions, etc. to couple respective ones of the deployable members 506 to the connecting arms 520. It should be noted, however, that the deployable members 506 could be coupled to the first ends 522 and second ends 524 of the connecting arms 520 through any suitable technique such as welding, adhesives, forming, machining, molding, etc. In one example, the connecting arms 520 can be fixed within the throughbores 514 to enable the deployable members 506 to move between the first, retracted position and the second, deployed position. However, it should be noted that the connecting arms 520 could be fixed relative to the deployable members 506 and rotatable relative to the throughbores 514 to enable the deployable members 506 to move between the first, retracted position and the second, deployed position.

Each of the deployable members 506 can be coupled to a respective one of the first ends 522 and the second ends 524 of the connecting arms 520. In one example, each of the deployable members 506 can include a first end 530 opposite a second end 532 and a bore 534. Generally, the first end 530 can taper to the second end 524. The bore 534 can comprise an elongated slot 534a, which can extend from the first end 530 to the second end 524, in one example, or the bore 534 can comprise a circular aperture 534b formed adjacent to the first end 530, as best shown in FIG. 20. The bore 534 can receive the respective first end 522 or second end 524 of one of the connecting arms 520 such that the cooperation between each of the connecting arms 520 and two of the deployable members 506 forms a respective U-shape adjacent to the proximal end 510 and the distal end 512 of the body 502.

In the example of the connecting arms 520 being fixed relative to the throughbores 514 (e.g. FIG. 18A), the slot 534a can move or slide relative to the first end 522 or second end 524 of the respective connecting arm 520 to move the deployable members 506 between the first, retracted position and the second, deployed position. In this regard, with the interspinous spacer 500 assembled, a suitable instrument can be used to move, advance or slide each of the deployable members 506 from the first, retracted position to the second, deployed position via the slidable engagement of the each of the slots 534a and the respective first end 522 and second end 524 of the connecting arms 520.

In the example of the connecting arms 520 being fixed relative to the respective deployable members 506 (e.g. FIGS. 18, 20), the deployable members 506 can rotate about the first end 522 or the second end 524 of the respective connecting arm 520 at a fixed location or fixed pivot point defined by the bore 534, such that the deployable members 506 can rotate clockwise or counterclockwise to move between the first, retracted position and the second, deployed position. In this regard, with the interspinous spacer 500 assembled, a suitable instrument can be used to rotate one of the deployable members 506 coupled at each of the proximal end 510 and distal end 512 of the body 502. As the connecting arms 520 are fixed relative to the deployable members 506, the rotation of one of the deployable members 506 from the first, retracted position to the second, deployed position can cause the other respective deployable member 506 to move from the first, retracted position and the second, deployed position.

Figure 21:
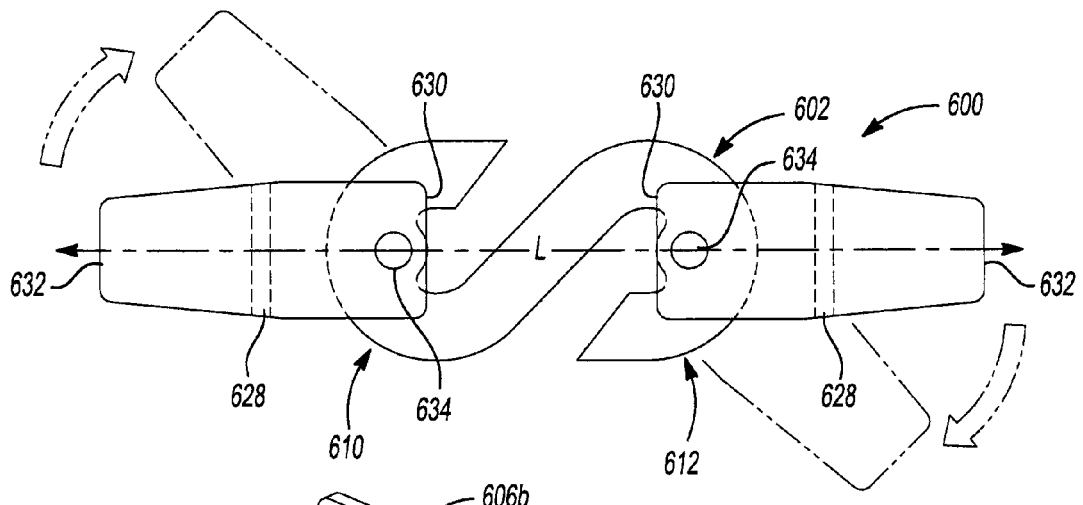
FIG. 21 is a schematic illustration of another exemplary interspinous spacer according to one of various teachings that is movable between a first, retracted state and a second, deployed state.
Figure 22:
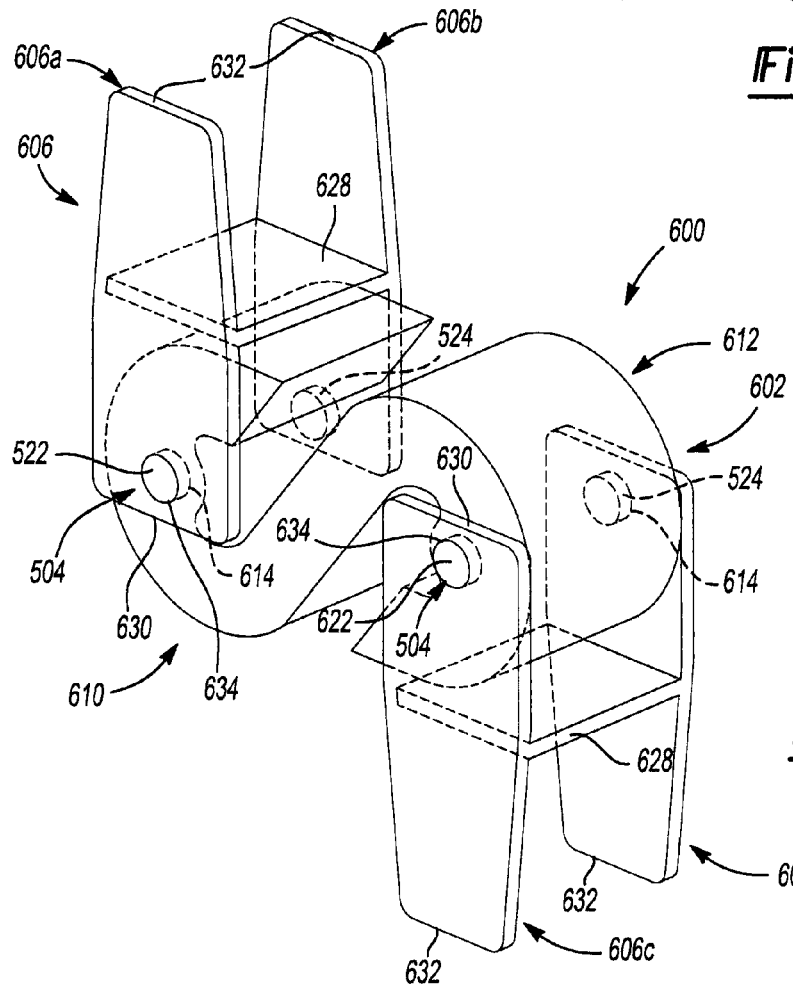
FIG. 22 is a schematic illustration of the interspinous spacer of FIG. 21 in the second, deployed state.

With reference to FIGS. 21-22, in another example, an interspinous spacer 600 can be employed to repair a damage portion of an anatomy. As the interspinous spacer 600 can be similar to the interspinous spacer 500 described with reference to FIGS. 18-20, only the differences between the interspinous spacer 500 and the interspinous spacer 600 will be discussed in great detail herein, and the same reference numerals will be used to denote the same or similar components. The interspinous spacer 600 can include a body 602, the actuator system 504 and at least one deployable member 606. In this example, the at least one deployable member 606 comprises four deployable members 606a, 606b, 606c, 606d, which will generally be referred to with the reference numeral 606. The actuator system 504 can cooperate with a suitable instrument to move the deployable members 606 from a first, retracted position (e.g., FIG. 21) to a second, deployed position (e.g., FIG. 22).

In one example, the body 602 can comprise a generally S-shaped body. The body 602 can be composed of any suitable biocompatible material, such as a biocompatible metal, metal alloy, polymer or combinations thereof, and for example, can be composed of polyetheretherketone (PEEK) or titanium. The body 602 can include a first or proximal end 610 and a second or distal end 612. Each of the proximal end 610 and the distal end 612 can define a throughbore 614. The throughbores 614 can extend in a direction generally transverse to a longitudinal axis L, and in one example, the throughbores 614 can extend in a direction generally perpendicular to the longitudinal axis L. The throughbores 614 can each receive a portion of the actuator system 604.

Each of the deployable members 606 can be coupled to the connecting arms 520. In one example, each of the deployable members 606 can include a first end 630 opposite a second end 632, and at least one bore 634. In this example, two of the deployable members 606 can be coupled together via a bridge member 628 such that each pair of deployable members 606 can form a substantially H-shape. The at least one bore 634 can formed adjacent to the first end 630. The bore 634 can be coupled to a respective one of the first ends 522 and the second ends 524 of the connecting arms 520 to enable the deployable members 606 to move between the first, retracted position and the second, deployed position.

In this regard, in one example, the connecting arms 520 can be fixed relative to the throughbores 614, and the deployable members 606 can move or rotate about the connecting arms 520 to move the deployable members 606 between the first, retracted position and the second, deployed position. In this regard, with the interspinous spacer 500 assembled, a suitable instrument can be used to move or rotate each of the deployable members 606 from the first, retracted position to the second, deployed position via rotating the deployable members 606 relative to the body 602.

In another of various examples, the connecting arms 520 can be fixed relative to the bores 634 of the respective deployable members 606 such that the connecting rod 520 can rotate within the throughbores 614, such that the deployable members 606 can rotate clockwise relative to the body 602 to move between the first, retracted position and the second, deployed position. In this regard, with the interspinous spacer 600 assembled, a suitable instrument can be used to rotate one of the deployable members 606 (or the connecting arms 520) coupled at each of the proximal end 610 and distal end 612 of the body 602. As the connecting arms 520 are fixed relative to the deployable members 606, the rotation of one of the deployable members 606 from the first, retracted position to the second, deployed position can cause the other respective deployable member 606 to move from the first, retracted position and the second, deployed position.

With reference to FIGS. 23-24, in another example, an interspinous spacer 650 can be employed to repair a damage portion of an anatomy. As the interspinous spacer 650 can be similar to the interspinous spacer 600 described with reference to FIGS. 21-22, only the differences between the interspinous spacer 600 and the interspinous spacer 650 will be discussed in great detail herein, and the same reference numerals will be used to denote the same or similar components. The interspinous spacer 650 can include the body 602, an actuator system 652 and the at least one deployable member 606. The actuator system 652 can cooperate with a suitable instrument to move the deployable members 606 from a first, retracted position (e.g., FIG. 23) to a second, deployed position (e.g., FIG. 24).

In one example, the actuator system 652 can comprise the connecting arms 520 and a linkage 660. The linkage 660 can be coupled to at least two of the deployable members 606. Generally, the linkage 660 can be coupled to one of the deployable members 606 coupled to the proximal end 610 of the body 602 and one of the deployable members 606 coupled to the distal end 612 of the body 602 so that all of the deployable members 606 can move substantially simultaneously. The linkage 660 can include ends 660a, 660b, which can be coupled together via a rod 660c. The ends 660a, 660b can be coupled to the deployable members 606 at any desired location, and in one example, the ends 660a, 660b can be coupled near the proximal end 610 of the respective deployable members 660. Generally, the ends 660a, 660b can be rotatably coupled to the deployable members 660, and in one example, the ends 660a, 660b can be fastened to the deployable members 606 so as to be rotatably retained by a mechanical fastener. It should be noted that although the linkage 660 is described and illustrated herein as being a discrete device, the linkage 660 could be integrally formed with the deployable members 660, if desired.

The linkage 660 can allow all of the deployable members 660 to move substantially simultaneously between the first, retracted position and the second, deployed position upon the movement of a single one of the deployable members 606. In this regard, with the interspinous spacer 650 assembled, a suitable instrument can be used to rotate one of the deployable members 606 (or the connecting arms 520) coupled at each of the proximal end 610 and distal end 612 of the body 602. As the deployable members 606 are coupled together via the linkage 660, the rotation of one of the deployable members 606 from the first, retracted position to the second, deployed position can cause the other respective deployable members 606 to move from the first, retracted position and the second, deployed position.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

For example, while the interspinous spacer 10 has been described herein as having resiliently deformable members 18 that are movable between a first, retracted position and a second, deployed position, those of skill in the art will appreciate that the present disclosure, in its broadest aspects, may be constructed somewhat differently. In this regard, with reference to FIGS. 25-26, an interspinous spacer 700 can include a body 702 and at least one deployable member 706. In this example, the at least one deployable member 706 comprises four deployable members 706a, 706b, 706c, 706d which will generally be referred to with the reference numeral 706. A suitable instrument can be used to move the deployable members 706 from a first, retracted position (e.g., FIG. 25) to a second, deployed position (e.g., FIG. 26).

The body 702 can comprise at least one bore 702. In this example, the body 702 can comprise two bores 702a, 702b. The bores 702a, 702b can comprise a pivot axis for each of the deployable members 706. Generally, each of the deployable members 706 can be rotatably coupled to the body 702 via an exemplary connecting arm, such as the connecting arm 520. The deployable members 706 can be movable relative to the body 702 between the first, retracted position and the second, deployed position, as will be discussed.

The deployable members 706 can be substantially similar, and can include a first or proximal end 710 and a second or distal end 712. Each proximal end 710 can define an aperture 710a, which can be used by a suitable instrument to move the deployable members 706 between the first, retracted position and the second, deployed position. The distal end 712 can comprise a bore 712a, which can rotatably couple the deployable members 706 to the body 702.

Figure 26:
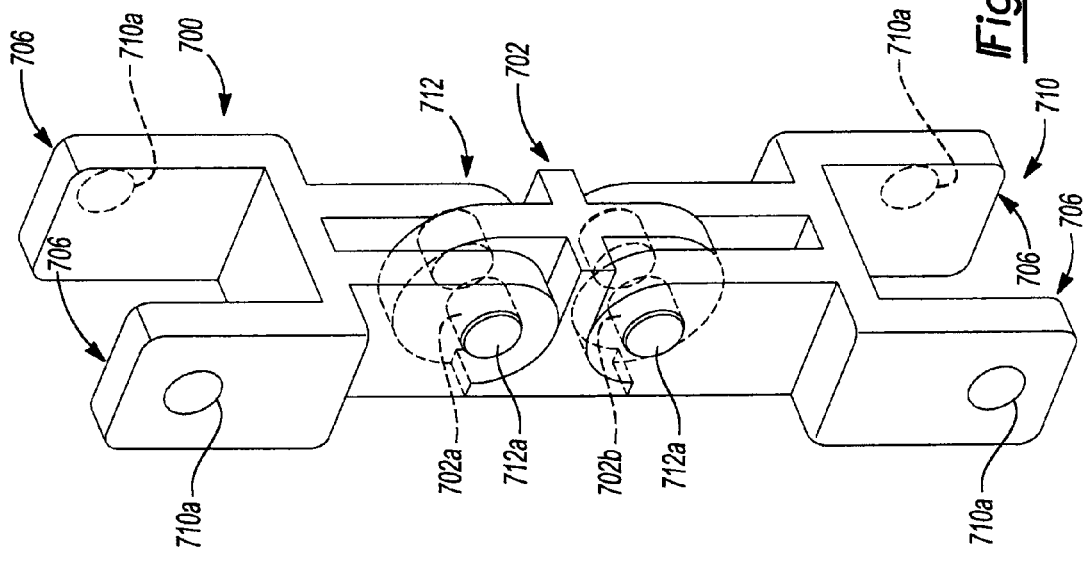
FIG. 26 is a schematic illustration of the interspinous spacer of FIG. 25 in the second, deployed state.
Figure 25:
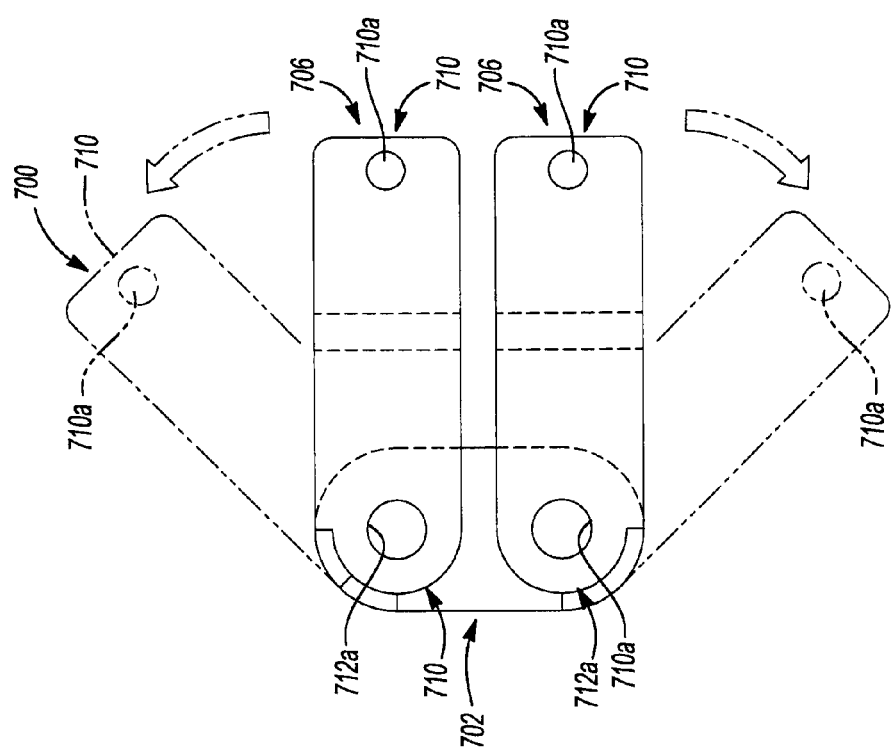
FIG. 25 is a schematic illustration of another exemplary interspinous spacer according to one of various teachings that is movable between a first, retracted state and a second, deployed state.

In this regard, each of the deployable members 706 can be coupled to the body 702 via the bore 712a. Generally, the deployable members 706 can be coupled to the body 702 so as to form a substantially square or rectangular shape in the first, retracted position (FIG. 25). The deployable members 706 can be rotated about the body 702 from the first, retracted position to the second, deployed position in which the deployable members 706 cooperate with the body 702 to form a substantially H-shaped interspinous spacer 700 (FIG. 26). In one example, a suitable instrument can engage each of the apertures 710a and move the respective one of the deployable members 706 from the first, retracted position to the second, deployed position.

Figure 28:
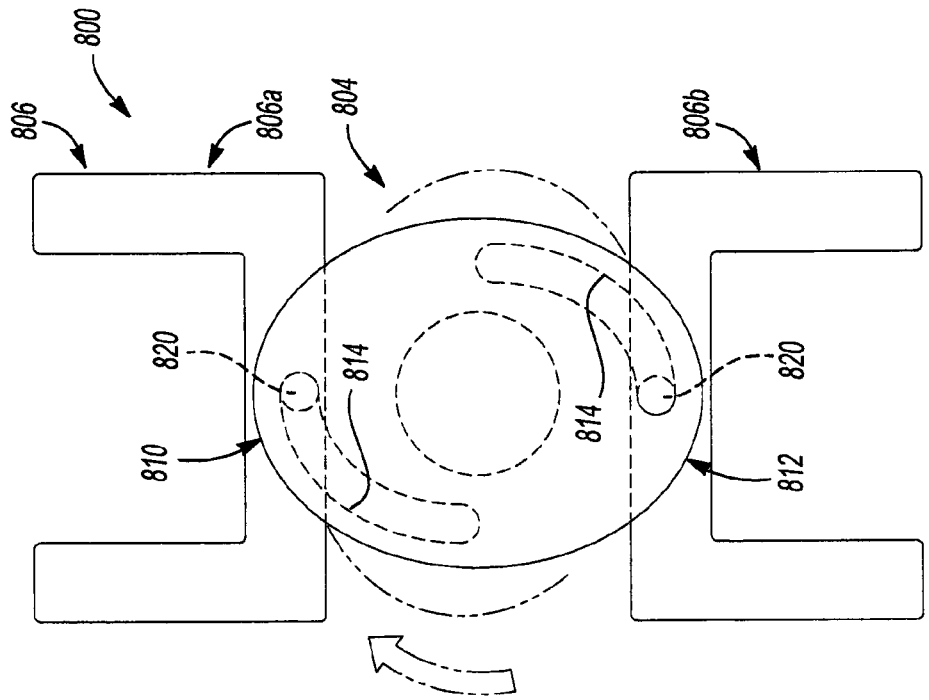
FIG. 28 is a schematic illustration of the interspinous spacer of FIG. 27 in the second, deployed state.
Figure 27:
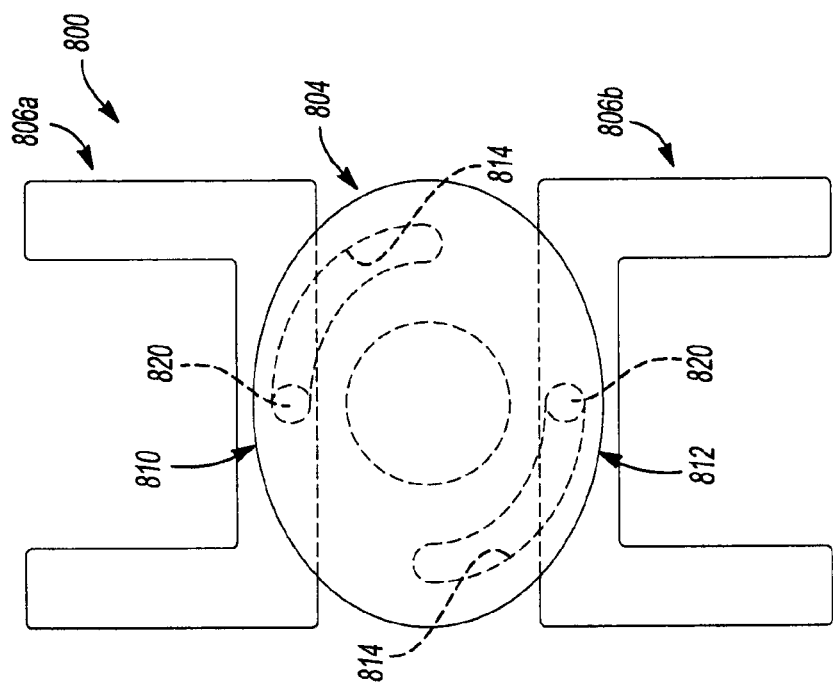
FIG. 27 is a schematic illustration of another exemplary interspinous spacer according to one of various teachings that is movable between a first, retracted state and a second, deployed state.

As a further example, with reference to FIGS. 27-28, an interspinous spacer 800 can include an actuator system 804 and at least one deployable member 806. In this example, the at least one deployable member 806 comprises two deployable members 806a, 806b, which will generally be referred to with the reference numeral 806. The actuator system 804 can cooperate with a suitable instrument to move the deployable members 806 from a first, retracted position (e.g., FIG. 27) to a second, deployed position (e.g., FIG. 28).

In one example, the actuator system 804 can comprise an annular or elliptical body, having a first end 810 and a second end 812. Each of the first end 810 and the second end 812 can include a slot 814. Each slot 814 can extend radially about at least a portion of the perimeter of the actuator system 804. Thus, the slots 814 can be arcuate in shape. The slots 814 can be sized to enable the deployable members 806 to move between the first, retracted position and the second, deployed position.

In this regard, each deployable member 806 can include a post 820, which can be slidably received within a respective one of the slots 814. Each of the deployable members 806 can be substantially U-shaped for positioning on opposite sides of a respective spinous process. The movement of the post 820 within the slot 814 can move a respective one of the deployable members 806 between the first, retracted position and the second, deployed position.

In this example, with the interspinous spacer 800 assembled, a suitable instrument can be used to move or rotate the actuator system 804, which can move, advance or slide the post 820 of each of the deployable members 806 in the slots 814 between the first, retracted position (e.g., FIG. 27) and the second, deployed position (e.g., FIG. 28).

What is claimed is:

1. An implant for insertion between adjacent spinous processes comprising:
   a body having a first end and a second end;
   a first deployable member extending between a first tip that is pivotally coupled to the first end of the body and a second tip that is spaced from the first tip of the first deployable member, the first deployable member movable relative to the body between a retracted position and a deployed position;
   a second deployable member extending between a first tip that is pivotally coupled to the second end of the body and a second tip that is spaced from the first tip of the second deployable member, the second deployable member movable relative to the body between a retracted position and a deployed position;
   a first cap pivotally coupled to the second tip of the first deployable member; and
   a second cap pivotally coupled to the second tip of the second deployable member and the second cap coupled to the first cap so that rotation of the first cap causes corresponding rotation of the second cap and the first and second deployable members between the retracted and deployed positions,
   wherein movement of the first and second deployable members between the retracted and deployed positions causes the first tips of the first and second deployable members to rotate relative to the body, the second tip of the first deployable member to rotate relative to the first cap, and the second tip of the second deployable member to rotate relative to the second cap.

2. The implant of claim 1, further comprising a third deployable member including a first tip pivotally coupled to the first end of the body and a second tip pivotally coupled to the first cap, the third deployable member movable with the first deployable member and the first cap between the retracted and deployed positions.

3. The implant of claim 2, further comprising a fourth deployable member including a first tip pivotally coupled to the second end of the body and a second tip pivotally coupled to the second cap, the fourth deployable member movable with the second deployable member and the second cap between the retracted and deployed positions.

4. The implant of claim 1, wherein movement from the retracted position to the deployed position includes a one-hundred-eighty-degree rotation of the first cap.

5. The implant of claim 1, in combination with a surgical insertion instrument coupled to the one of the first cap or the second cap and the body to rotate the one of the first cap or the second cap relative to the body to substantially simultaneously move the first deployable member and the second deployable member from the retracted position to the deployed position.

6. The implant of claim 1, wherein the body has a first surface and a second opposite surface, and the first surface and the second surface have a bicone taper that is adapted to center a respective spinous process on the first surface and the second surface.

7. The implant of claim 6, wherein the body includes a longitudinally extending body with the first end at one longitudinal end of the body and the second end at an opposite longitudinal end of the body, the first and second surfaces extending between the first and second ends.

8. The implant of claim 7, wherein the body includes:
an upper surface and an opposite lower surface, the upper and lower surfaces extending between the first and second ends;
a first slot formed in the body from a first side thereof and extending between the first and second ends; and
a second slot formed in the body from a second side opposite the first side thereof and extending between the first and second ends;
wherein the first and second slots cooperate to allow the body to flex so as to be adapted to flex based on movement of the adjacent spinous processes.

9. The implant of claim 8, wherein the first slot is formed adjacent the first surface and extends from the first side toward the second side, and wherein the second slot is formed adjacent the second surface and extends from the second side toward the first side such that the first and second slots cooperate with the body to form an S-shape.

10. The implant of claim 1, wherein one of the first and second caps tapers to a point to guide the implant into a patient's anatomy.

11. An implant for insertion between adjacent spinous processes comprising:
a body having a first end and a second end;
a cap coupled to the first end of the body, the cap and the first end defining a space therebetween;
a first deployable member received within the space and coupled to the first end of the body, the first deployable member being movable within the space and the first deployable member movable relative to the body between a retracted position and a deployed position, wherein at least a majority of the first deployable member is stored in the space in the retracted position and swings out from the space in the deployed position; and
a second deployable member coupled to the second end of the body and movable relative to the body between a retracted position and a deployed position;
wherein rotation of the cap causes corresponding rotation of the first and second deployable members between the retracted and deployed positions.

12. The implant of claim 11, wherein the first and second deployable members extend from the body in opposite directions when in the deployed positions.

13. The implant of claim 11, further comprising a third deployable member coupled to the first end of the body and the cap and movable with the first deployable member and the cap between the retracted and deployed positions.

14. The implant of claim 13, further comprising a fourth deployable member coupled to the second end of the body and movable with the second deployable member between the retracted and deployed positions.

15. The implant of claim 11, wherein movement from the retracted position to the deployed position includes a one-hundred-eighty-degree rotation of the cap.

16. The implant of claim 11, in combination with a surgical insertion instrument coupled to the cap and the body to rotate the cap relative to the body to substantially simultaneously move the first deployable member and the second deployable member from the retracted position to the deployed position.

17. The implant of claim 11, wherein the body has a first surface and a second opposite surface, and the first surface and the second surface have a bicone taper that is adapted to center a respective spinous process on the first surface and the second surface.

18. The implant of claim 17, wherein the body includes a longitudinally extending body with the first end at one longitudinal end of the body and the second end at an opposite longitudinal end of the body, the first and second surfaces extending between the first and second ends.

19. The implant of claim 18, wherein the body includes:
an upper surface and an opposite lower surface, the upper and lower surfaces extending between the first and second ends;
a first slot formed in the body from a first side thereof and extending between the first and second ends; and
a second slot formed in the body from a second side opposite the first side thereof and extending between the first and second ends;
wherein the first and second slots cooperate to allow the body to flex so as to be adapted to flex based on movement of the adjacent spinous processes.

20. The implant of claim 19, wherein the first slot is formed adjacent the first surface and extends from the first side toward the second side, and wherein the second slot is formed adjacent the second surface and extends from the second side toward the first side such that the first and second slots cooperate with the body to form an S-shape.

21. The implant of claim 11, further comprising another cap coupled to the second deployable member, wherein movement of one of the caps causes corresponding movement of the other cap and the first and second deployable members between the retracted and deployed positions.

22. The implant of claim 1, wherein the body includes a first bore that receives the first tip of the first deployable member and a second bore that receives the first tip of the second deployable member, the first cap includes a first recess that receives the second tip of the first deployable member, and the second cap includes a second recess that receives the second tip of the second deployable member.

23. The implant of claim 1, wherein the first tip of the first deployable member is directly pivotally coupled to the first end of the body, the second tip of the first deployable member is directly pivotally coupled to the first cap, the first tip of the second deployable member is directly pivotally coupled to the second end of the body, and the second tip of the second deployable member is directly pivotally coupled to the second cap.

24. The implant of claim 1, wherein the first cap and the first end of the body define a first space therebetween that receives at least a portion of the first deployable member and the second cap and the second end of the body define a second space therebetween that receives at least a portion of the second deployable member, the first and second tips of the first deployable member disposed in the first space, and the first and second tips of the second deployable member disposed in the second space.

25. The implant of claim 11, wherein the first deployable member extends between a first tip and a second tip, the first and second tips disposed in the space between the cap and the first end of the body.

* * * * *